(12) United States Patent
Alterman et al.

(10) Patent No.: US 8,124,638 B2
(45) Date of Patent: Feb. 28, 2012

(54) TRICYCLIC COMPOUNDS USEFUL AS ANGIOTENSIN II AGONISTS

(75) Inventors: Mathias Alterman, Stockholm (SE); Anders Rudolf Hallberg, Stockholm (SE)

(73) Assignee: Vicore Pharma AB, Uppsala (SE)

( * ) Notice: Subject to any disclaimer, the term of this patent is extended or adjusted under 35 U.S.C. 154(b) by 0 days.

(21) Appl. No.: 12/553,939

(22) Filed: Sep. 3, 2009

(65) Prior Publication Data

US 2009/0326026 A1 Dec. 31, 2009

Related U.S. Application Data

(63) Continuation of application No. 10/721,892, filed on Nov. 26, 2003, now Pat. No. 7,652,054, which is a continuation-in-part of application No. PCT/GB02/02563, filed on May 30, 2002, now abandoned.

(60) Provisional application No. 60/350,959, filed on Jan. 25, 2002.

(30) Foreign Application Priority Data

| May 31, 2001 | (GB) | ................................... | 0113129.1 |
| Sep. 7, 2001 | (GB) | ................................... | 0121611.8 |
| Jan. 26, 2002 | (GB) | ................................... | 0201794.5 |

(51) Int. Cl.
*A61K 31/4178* (2006.01)

(52) U.S. Cl. ....................................................... 514/396

(58) Field of Classification Search ........................ None
See application file for complete search history.

(56) References Cited

U.S. PATENT DOCUMENTS

| 5,091,390 A | 2/1992 | Ardecky et al. |
| 5,166,206 A | 11/1992 | Allen et al. |
| 5,177,074 A | 1/1993 | Allen et al. |
| 5,198,438 A | 3/1993 | Allen et al. |
| 5,240,928 A | 8/1993 | Allen et al. |
| 5,250,521 A | 10/1993 | Allen et al. |
| 5,252,574 A | 10/1993 | Allen et al. |
| 5,260,285 A | 11/1993 | Allen et al. |
| 5,312,820 A | 5/1994 | Ashton et al. |
| 5,330,987 A | 7/1994 | Allen et al. |
| 5,376,666 A | 12/1994 | Duncia |
| 5,412,097 A | 5/1995 | Chakravarty et al. |
| 5,444,067 A | 8/1995 | Kivlighn et al. |
| 5,807,878 A | 9/1998 | Corbier et al. |
| 5,834,432 A | 11/1998 | Rodgers et al. |
| 5,932,575 A | 8/1999 | Yanaka et al. |
| 6,235,766 B1 | 5/2001 | Heitsch et al. |
| 6,335,451 B1 | 1/2002 | Kleemann et al. |

FOREIGN PATENT DOCUMENTS

| EP | 0 409 332 A2 | 1/1991 |
| EP | 0 512 675 A1 | 11/1992 |
| WO | WO 94/02142 | 2/1994 |
| WO | WO 94/03435 | 2/1994 |
| WO | WO 94/27597 | 12/1994 |
| WO | WO 95/23792 | 9/1995 |
| WO | WO 98/33813 | 8/1998 |
| WO | WO 99/26644 | 6/1999 |
| WO | WO 99/39743 | 8/1999 |
| WO | WO 99/40106 | 8/1999 |
| WO | WO 99/40107 | 8/1999 |
| WO | WO 99/42122 | 8/1999 |
| WO | WO 99/43339 | 9/1999 |
| WO | WO 99/45945 | 9/1999 |
| WO | WO 99/46285 | 9/1999 |
| WO | WO 99/52540 | 10/1999 |
| WO | WO 99/58140 | 11/1999 |
| WO | WO 00/02905 | 1/2000 |
| WO | WO 00/09144 | 2/2000 |
| WO | WO 00/38676 | 7/2000 |
| WO | WO 00/56345 | 9/2000 |
| WO | WO 00/68226 | 11/2000 |
| WO | WO 01/44239 | 6/2001 |

OTHER PUBLICATIONS

Golub et al., Science, vol. 286, Oct. 15, 1999, pp. 531-537.*
Ardaillou, "Angiotensin II Receptors" *J. Am. Soc. Nephrol.* 10:S30-S39 (1999).
Gasparo, M. et al., "International Union of Pharmacology. XXIII. The Angiotensin II Receptors", *Pharmacol. Rev.* 52:415-72 (2000).

* cited by examiner

*Primary Examiner* — Laura L. Stockton
(74) *Attorney, Agent, or Firm* — Finnegan, Henderson, Farabow, Garrett & Dunner LLP

(57) ABSTRACT

There is provided compounds of formula (I), wherein $X_1$, $X_2$, $X_3$, $Y_4$, $Y_1$, $Y_2$, $Y_3$, $Y_4$, $Z_1$, $Z_2$, $R^4$ and $R^5$ have meanings given in the description, and pharmaceutically-acceptable salts thereof, which compounds are useful as selective agonists of the AT2 receptor, and thus, in particular, in the treatment of inter alia gastrointestinal conditions, such as dyspepsia, IBS and MOF, and cardiovascular disorders.

2 Claims, No Drawings

TRICYCLIC COMPOUNDS USEFUL AS ANGIOTENSIN II AGONISTS

This application is a continuation of Application Ser. No. 10/721,892, filed Nov. 26, 2003, now U.S. Pat. No. 7,652,054, which is a continuation-in-part of International Application PCT/GB02/02563, with an international filing date of May 30, 2002, now abandoned, the entirety of which is hereby incorporated by reference herein, which claims the benefit of each of GB applications 0113129.1, filed May 31, 2001, 0121611.8, filed Sep. 7, 2001, 0201794.5, filed Jan. 26, 2002, each of which is hereby incorporated by reference herein in its entirety, and which also claims the benefit of U.S. Provisional Application No. 60/350,959, filed Jan. 25, 2002, the entirety of which is hereby incorporated by reference herein.

FIELD OF THE INVENTION

This invention relates to novel pharmaceutically-useful compounds, in particular compounds that are angiotensin II (AngII) agonists, more particularly agonists of the AngII type 2 receptor (hereinafter the AT2 receptor), and especially agonists that bind selectively to that receptor. The invention further relates to the use of such compounds as medicaments, to pharmaceutical compositions containing them, and to synthetic routes to their production.

BACKGROUND AND PRIOR ART

The endogenous hormone AngII is a linear octapeptide ($Asp^1$-$Arg^2$-$Val^3$-$Tyr^4$-$Ile^5$-$His^6$-$Pro^7$-$Phe^8$), and is the active component of the renin-angiotensin system (RAS). It is produced by the sequential processing of the pro-hormone angiotensinogen by renin and angiotensin converting enzyme (ACE).

The renin-angiotensin system (RAS) plays an important role in the regulation of blood pressure, body fluid and electrolyte homeostasis. Ang II exerts these physiological actions in many organs including the kidneys, the adrenal glands, the heart, blood vessels, the brain, the gastrointestinal tract and the reproductive organs (de Gasparo et al, *Pharmacol. Rev.* (2000) 52, 415-472).

Two main classes of AngII receptors have been identified, and designated as the type 1 receptor (hereinafter the AT1 receptor) and the AT2 receptor.

The AT1 receptor is expressed in most organs, and is believed to be responsible for the majority of the biological effects of AngII. The AT2 receptor is more prevalent than the AT1 receptor in fetal tissues, the adult ovaries, the adrenal medulla and the pancreas. An equal distribution is reported in the brain and uterus (Ardaillou, *J. Am. Soc. Nephrol.*, 10, S30-39 (1999)).

Several studies in adult individuals appear to demonstrate that, in the modulation of the response following AngII stimulation, activation of the AT2 receptor has opposing effects to those mediated by the AT1 receptor.

The AT2 receptor has also been shown to be involved in apoptosis and inhibition of cell proliferation (see de Gasparo et al, supra). Further, it seems to play a role in blood pressure control. For example, it has been shown in transgenic mice lacking AT2 receptors that their blood pressure was elevated. Furthermore, it has been concluded that the AT2 receptor is involved in exploratory behaviour, pain sensitivity and thermoregulation.

The expression of AT2 receptors has also been shown to increase during pathological circumstances, such as vascular injury, wound healing and heart failure (see de Gasparo et al, supra).

The expected pharmacological effects of agonism of the AT2 receptor are described generally in de Gasparo et al, supra.

More recently, AT2 receptor agonists have been shown to be of potential utility in the treatment and/or prophylaxis of disorders of the alimentary tract, such as dyspepsia and irritable bowel syndrome, as well as multiple organ failure (see international patent application WO 99/43339).

AngII antagonists (which bind to the AT1 and/or AT2 receptors) have been disclosed in inter alia European patent applications EP 409 332, EP 512 675; international patent applications WO 94/27597, WO 94/02142, WO 95/23792 and WO 94/03435; and U.S. Pat. Nos. 5,091,390, 5,177,074, 5,412,097, 5,250,521, 5,260,285, 5,376,666, 5,252,574, 5,312,820, 5,330,987, 5,166,206, 5,932,575 and 5,240,928. AngII agonists, and particularly AT2 receptor agonists, are not contemplated in any of these documents.

International patent application WO 00/68226 and U.S. Pat. No. 6,235,766 disclose compounds comprising substituted imidazolyl groups, which groups are attached, via a methylene bridge, to a phenylthiophene moiety, as agonists of angiotensin-(1-7) receptors. International patent application WO 01/44239 discloses biphenylsulfonamide compounds as combined angiotensin and endothelin receptor antagonists. The use of the compounds as Ang II receptor agonists is neither mentioned nor suggested in any of these documents.

U.S. Pat. No. 5,444,067 discloses compounds comprising a 5,7-dimethyl-2-ethylpyridinoimidazolyl group attached, via a methylene bridge, to a phenylthiophene moiety, as AT2 receptor agonists. The use of unsubstituted imidazole-containing compounds is neither mentioned nor suggested.

Peptide and non-peptide AT2 receptor agonists, unrelated structurally to those described herein, and potential uses thereof, have been disclosed in, for example, international patent applications WO 00/38676, WO 00/56345, WO 00/09144, WO 99/58140, WO 99/52540, WO 99/46285, WO 99/45945, WO 99/42122, WO 99/40107, WO 99/40106, WO 99/39743, WO 99/26644, WO 98/33813, WO 00/02905 and WO 99/46285; U.S. Pat. No. 5,834,432; and Japanese patent application JP 143695.

However, there remains a need for effective and/or selective AT2 receptor agonists, which are expected to find utility in inter alia the above-mentioned conditions.

DISCLOSURE OF THE INVENTION

According to the invention there is provided a compound of formula I,

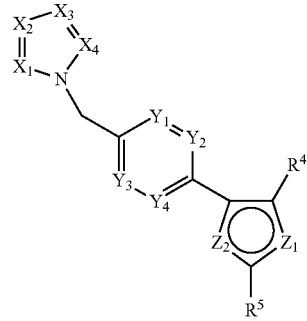

wherein
one of $X_1$ and $X_2$ represents —N— and the other represents —C($R^1$)—;
$X_3$ represents —N— or —C($R^2$)—;
$X_4$ represents —N— or —C($R^3$)—;
$R^1$, $R^2$ and $R^3$ independently represent H, $C_{1-6}$ alkyl, $C_{1-6}$ alkoxy, $C_{1-6}$ alkoxy-$C_{1-6}$-alkyl or halo;

provided that, when $X_1$ represents —C($R^1$)—, $X_3$ represents —C($R^2$)— and $X_4$ represents —C($R^3$)—, then $R^1$ represents H;

$Y_1$, $Y_2$, $Y_3$ and $Y_4$ independently represent —CH— or —CF—;

$Z_1$ represents —CH—, —O—, —S—, —N— or —CH=CH—;

$Z_2$ represents —CH—, —O—, —S— or —N—;

provided that:
(a) $Z_1$ and $Z_2$ are not the same;
(b) when $Z_1$ represents —CH=CH—, then $Z_2$ may only represent —CH— or —N—; and
(c) other than in the specific case in which $Z_1$ represents —CH=CH—, and $Z_2$ represents —CH—, when one $Z_1$ and $Z_2$ represents —CH—, then the other represents —O— or —S—;

$R^4$ represents —S(O)$_2$N(H)C(O)$R^6$, —S(O)$_2$N(H)S(O)$_2R^6$, —C(O)N(H)S(O)$_2R^6$, or, when $Z_1$ represents —CH=CH—, $R^4$ may represent —N(H)S(O)$_2$N(H)C(O)$R^7$ or —N(H)C(O)N(H)S(O)$_2R^7$;

$R^5$ represents $C_{1-6}$ alkyl, $C_{1-6}$ alkoxy, $C_{1-6}$ alkoxy-$C_{1-6}$-alkyl or di-$C_{1-3}$-alkylamino-$C_{1-4}$-alkyl;

$R^6$ represents $C_{1-6}$ alkyl, $C_{1-6}$ alkoxy, $C_{1-6}$ alkoxy-$C_{1-4}$-alkyl, $C_{1-3}$ alkoxy-$C_{1-6}$-alkoxy, $C_{1-6}$ alkylamino or di-$C_{1-6}$ alkylamino; and $R^7$ represents $C_{1-6}$ alkyl, or a pharmaceutically-acceptable salt thereof, which compounds and salts are referred to together hereinafter as "the compounds of the invention".

Pharmaceutically-acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion, for example using a suitable ion exchange resin.

Unless otherwise specified, alkyl groups, and the alkyl parts of alkoxy, alkoxyalkyl, alkoxyalkoxy, alkylamino and alkylaminoalkyl groups, as defined herein may be straight-chain or, when there is a sufficient number (i.e. a minimum of three) of carbon atoms, be branched-chain, and/or cyclic. Further, when there is a sufficient number (i.e. a minimum of four) of carbon atoms, such groups may also be part cyclic/acyclic. Such alkyl groups, and alkyl parts of alkoxy, alkoxyalkyl, alkoxyalkoxy, alkylamino and alkylaminoalkyl groups, may also be saturated or, when there is a sufficient number (i.e. a minimum of two) of carbon atoms, be unsaturated. Unless otherwise specified, such groups may also be substituted by one or more halo, and especially fluoro, atoms.

For the avoidance of doubt, alkoxy and alkoxyalkoxy groups are attached to the rest of the molecule via the oxygen atom in that group, alkylamino groups are attached to the rest of the molecule via the nitrogen atom of the amino part of that group and alkylaminoalkyl and alkoxyalkyl groups are attached to the rest of the molecule via the alkyl part of that group.

The term "halo", when used herein, includes fluoro, chloro, bromo and iodo.

Preferred ring systems comprising the substituents $Y_1$, $Y_2$, $Y_3$ and $Y_4$ include phenyl groups. For the avoidance of doubt, the ring systems in compounds of formula I that comprise the groups $Z_1$ and $Z_2$, are aromatic in nature. In some instances, for example in cases where one or more of $Z_1$ and $Z_2$ represent —CH— or —N— the skilled person will appreciate that an additional H atom may necessarily be bonded to that CH group or N atom, in order to ensure that the rules of valency are adhered to. Preferred ring systems comprising $Z_1$ and $Z_2$ include oxazole groups, thiazole groups, phenyl groups, pyridinyl groups, thiophenyl groups and furanyl groups.

In this respect, compounds of the invention may exhibit tautomerism. All tautomeric forms and mixtures thereof are included within the scope of the invention.

Compounds of the invention also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Preferred compounds of the invention include those in which:
(i) when $X_1$ represents —C($R^1$)—, then:
(a) $X_3$ represents —C($R^2$)— and $X_4$ represents —N—;
(b) $X_3$ and $X_4$ both represent N; or
(c) $X_3$ represents —C($R^2$)— and $X_4$ represents —C($R^3$)—; or
(ii) when $X_1$ represents —N—, then
(a) $X_3$ represents —N—; or
(b) $X_3$ represents —C($R^2$) and $X_4$ represents —C($R^3$)—.

In case (i)(a) above, it is further preferred that $R^1$ represents H.

In case (ii)(a) above, when $X_4$ represents —C($R^3$)—, it is further preferred that $R^3$ represents H.

Preferred compounds of formula I include those in which:
$R^1$ represents $C_{1-3}$ allyl, such as ethyl, —CF$_3$ or, especially, H;
$R^2$ represents $C_{1-3}$ alkyl, such as methyl, halo, or, especially, H;
$R^3$ represents $C_{1-3}$ alkyl, halo or, especially, H;
$Y_1$, $Y_2$, $Y_3$ and $Y_4$ all represent —CH—;
$Z_1$ represents —S— or —CH=CH—;
$Z_2$ represents —CH—;
$R^4$ represents S(O)$_2$N(H)C(O)$R^6$;
$R^5$ represents n-butyl or, particularly, iso-butyl;
$R^6$ represents n-butoxymethyl, iso-butoxy and especially, n-butoxy.

Preferred ring systems comprising the substituents $X_1$, $X_2$, $X_3$ and $X_4$ include pyrazole groups, imidazole groups, 1,2,4-triazole groups and tetrazole groups.

Compounds of the invention that may be mentioned include those in which, when $X_1$, $X_3$ and $X_4$ all represent —CH—, $Y_1$, $Y_2$, $Y_3$ and $Y_4$ all represent —CH—, $Z_1$ represents —CH=CH— or, particularly, —S—, $Z_2$ represents —CH— and $R^5$ represents n-butyl or, particularly, iso-butyl, then $R^4$ represents —S(O)$_2$N(H)C(O)$R^6$, in which $R^6$ represents —O-iso-propyl (i.e. iso-propoxy), —O-iso-butyl (i.e. iso-butoxy), —CH$_2$—O-n-butyl (i.e. n-butoxymethyl) or, particularly, —O-n-butyl (i.e. n-butoxy).

Compounds of the invention that may farther be mentioned include those in which, when $X_1$, $X_3$ and $X_4$ all represent —CH—, $Y_1$, $Y_2$, $Y_3$ and $Y_4$ all represent —CH—, $Z_1$ represents —CH=CH— or —S—, $Z_2$ represents —CH— and $R^5$ represents n-butyl or iso-butyl, then $R^4$ does not represent —S(O)$_2$N(H)C(O)R$^6$, in which R$^6$ represents —O-iso-propyl, —O-iso-butyl, —CH$_2$—O-n-butyl or —O-n-butyl.

Further compounds of the invention that may be mentioned include those in which:
R$^4$ does not represent —S(O)$_2$N(H)S(O)$_2$R$^6$;
R$^5$ does not represent di-C$_{1-3}$ alkylamino-C$_{1-4}$-alkyl;
R$^6$ does not represent C$_{1-3}$ alkoxy-C$_{1-6}$ alkoxy.

More preferred compounds of the invention include the compounds of the examples described hereinafter.

Compounds of formula I may be made in accordance with techniques well known to those skilled in the art, for example as described hereinafter.

According to a further aspect of the invention there is provided a process for the preparation of a compound of formula I, which process comprises:
(i) for compounds of formula I in which R$^4$ represents —S(O)$_2$N(H)C(O)R$^6$ or —S(O)$_2$N(H)S(O)$_2$R$^6$, and R$^6$ is as hereinbefore defined, reaction of a compound of formula II,

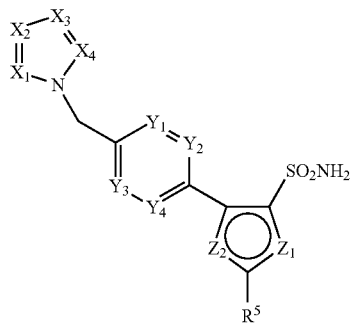

II wherein X$_1$, X$_2$, X$_3$, X$_4$, Y$_1$, Y$_2$, Y$_3$, Y$_4$, Z$_1$, Z$_2$ and R$^5$ are as hereinbefore defined with a compound of formula III,

R$^6$GL$^1$  III wherein G represents C(O) or S(O)$_2$ (as appropriate), L$^1$ represents a suitable leaving group, such as halo (e.g. chloro or bromo) and R$^6$ is as hereinbefore defined, for example at around room temperature or above (e.g. up to 60-70° C.) in the presence of a suitable base (e.g. pyrollidinopyridine, pyridine, triethylamine, tributylamine, trimethylamine, dimethylaminopyridine, di-iso-propylamine, 1,8-diazabicyclo[5.4.0]undec-7-ene, sodium hydroxide, or mixtures thereof) and an appropriate solvent (e.g. pyridine, dichloromethane, chloroform, tetrahydrofuran, dimethylformamide, trifluoromethylbenzene or triethylamine). Preferred base/solvent systems for compounds of formula III in which G is C(O) include pyrollidinopyridine/pyridine, pyrollidinopyridine/triethylamine, dimethylaminopyridine/pyridine or dimethylaminopyridine/triethylamine. Preferred base/solvent systems for compounds of formula III in which G is S(O)$_2$ include NaOH/THF;

(ii) for compounds of formula I in which R$^4$ represents —S(O)$_2$N(H)C(O)R$^6$ and R$^6$ represents C$_{1-6}$ alkoxy-C$_{1-6}$-alkyl, coupling of a compound of formula II as hereinbefore defined with a compound of formula V, R$^{6a}$CO$_2$H  IV wherein R$^{6a}$ represents C$_{1-6}$ alkoxy-C$_{1-6}$-alkyl, for example under similar conditions to those described under process step (i) above, in the presence of a suitable coupling reagent (e.g. 1,1'-carbonyl-diimidazole, N,N'-dicyclohexylcarbodiimide, N,N'-disuccinimidyl carbonate, benzotriazole-1-yloxytris(dimethylamino)phosphoniumhexafluorophosphate, 2-(1H-benzotriazole-1-yl)-1,1,3,3-tetramethyluronium hexafluorophosphate, benzotriazole-1-yl-oxy-tris-pyrrolidino-phosphonium hexafluorophosphate, bromo-tris-pyrrolidinophosponium hexafluorophosphate or 2-(1H-benzotriazole-1-yl)-1,1,3,3-tetramethyluronium tetrafluorocarbonate), a suitable base (as mentioned in process step (i) above) and an appropriate solvent (as mentioned in process step (i) above);

(iii) for compounds of formula I in which R$^4$ represents —C(O)N(H)S(O)$_2$R$^6$ and R$^6$ is as hereinbefore defined, coupling of a compound of formula V,

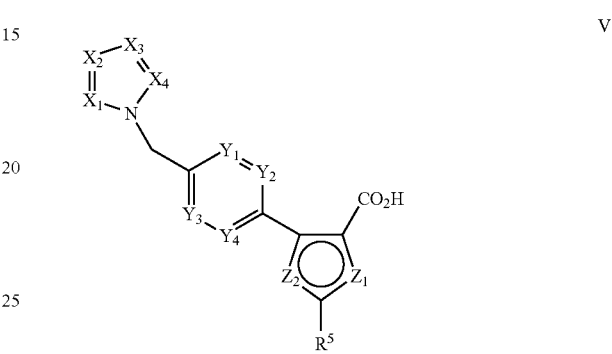

V wherein X$_1$, X$_2$, X$_3$, X$_4$, Y$_1$, Y$_2$, Y$_3$, Y$_4$, Z$_1$, Z$_2$ and R$^5$ are as hereinbefore defined with a compound of formula VI,

R$^6$S(O)$_2$NH$_2$  VI wherein R$^6$ is as hereinbefore defined, for example in the presence of a suitable coupling reagent (such as those described in process step (ii) hereinbefore), and under similar reaction conditions to those described hereinbefore for preparation of compounds of formula I in which R$^6$ represents C$_{1-6}$ alkoxy-C$_{1-6}$-alkyl;

(iv) for compounds of formula I in which R$^4$ represents —C(O)N(H)S(O)$_2$R$^6$ and R$^6$ is as hereinbefore defined, coupling of a compound of formula VII,

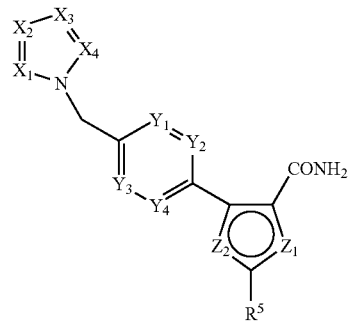

VII wherein X$_1$, X$_2$, X$_3$, X$_4$, Y$_1$, Y$_2$, Y$_3$, Y$_4$, Z$_1$, Z$_2$ and R$^5$ are as hereinbefore defined with a compound of formula VIII, R$^6$S(O)$_2$Cl  VIII wherein R$^6$ is as hereinbefore defined, for example at around 50° C. in the presence of a suitable base (e.g. sodium hydride) and an appropriate organic solvent (e.g. THF);

(v) for compounds of formula I in which $R^4$ represents —N(H)S(O)$_2$N(H)C(O)R$^7$ and $R^7$ is as hereinbefore defined, reaction of a compound of formula IX,

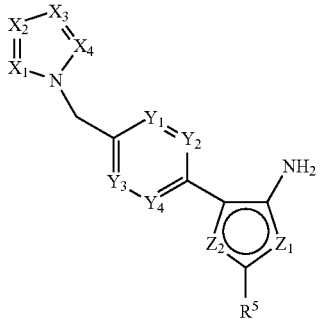

wherein $X_1$, $X_2$, $X_3$, $X_4$, $Y_1$, $Y_2$, $Y_3$, $Y_4$, $Z_1$, $Z_2$ and $R^5$ are as hereinbefore defined with a compound of formula X, $$R^7C(O)N(H)S(O)_2Cl \qquad X$$

wherein $R^7$ is as hereinbefore defined, for example at or around room temperature in the presence of a suitable base (e.g. sodium hydroxide or triethylamine) and a suitable organic solvent (e.g. benzene or dichloromethane);

(vi) for compounds of formula I in which $R^4$ represents —N(H)C(O)N(H)S(O)$_2$R$^7$ and $R^7$ is as hereinbefore defined, reaction of a compound of formula IX as hereinbefore defined with a compound of formula XI, $$R^7S(O)_2N(H)C(O)OR^x \qquad XI$$

wherein $R^x$ represents $C_{1-2}$ alkyl and $R^7$ is as hereinbefore defined, for example at or around room temperature in the presence of a suitable organic solvent (e.g. dichloromethane);

(vii) for compounds of formula I in which $R^4$ represents —N(H)C(O)N(H)S(O)$_2$R$^7$ and $R^7$ is as hereinbefore defined, reaction of a compound of formula IX as hereinbefore defined with an isocyanate compound of formula XII, $$R^7S(O)_2NCO \qquad XII$$

wherein $R^7$ is as hereinbefore defined, for example at or around room temperature in the presence of a suitable organic solvent (e.g. dichloromethane);

(viii) for compounds of formula I in which $R^4$ represents —S(O)$_2$N(H)C(O)R$^6$ and $R^6$ represents $C_{1-6}$ alkylamino, reaction of a compound of formula II as hereinbefore defined with an isocyanate compound of formula XIII, $$R^{6b}NCO \qquad XIII$$

wherein $R^{6b}$ is $C_{1-6}$ alkyl, for example at or around room temperature in the presence of a suitable base (e.g. sodium hydroxide or potassium hydroxide and an appropriate organic solvent (e.g. acetone or acetonitrile); or (ix) for compounds of formula I in which $R^4$ represents —S(O)$_2$N(H)C(O)R$^6$ and $R^6$ represents di-$C_{1-6}$ alkylamino, reaction of a corresponding compound of formula I in which $R^4$ represents —S(O)$_2$N(H)C(O)R$^6$ and $R^6$ represents $C_{1-6}$ alkoxy with an amine of formula XIV, $$R^{6c}N(H)R^{6d} \qquad XIV$$

wherein $R^{6c}$ and $R^{6d}$ independently represent $C_{1-6}$ alkyl, for example at above room temperature (e.g. at between 70° C. and 100° C.) in the presence of an appropriate organic solvent (e.g. toluene).

Compounds of formula II may be prepared by reaction of a compound of formula XV,

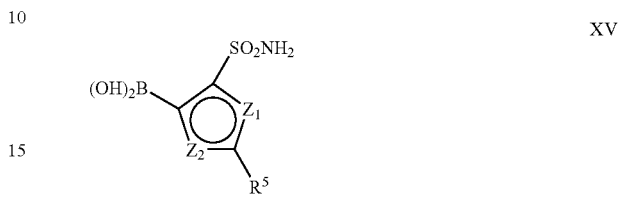

wherein $R^5$, $Z^1$ and $Z^2$ are as hereinbefore defined, or a N-protected derivative thereof, with a compound of formula XVI,

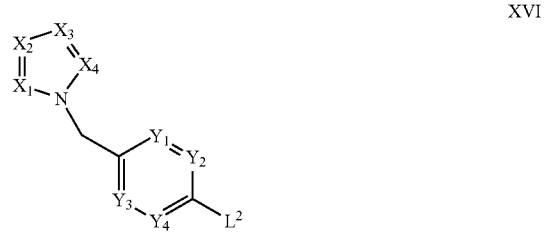

wherein $L^2$ represents a suitable leaving group, such as trimethylsulphonate, or halo, such as iodo or bromo, and $X_1$, $X_2$, $X_3$, $X_4$, $Y_1$, $Y_2$, $Y_3$ and $Y_4$ are as hereinbefore defined, for example in the presence of an appropriate coupling catalyst system (e.g. a palladium catalyst, such as Pd(PPh$_3$)$_4$ or Pd(OAc)$_2$/ligand (wherein the ligand may be, for example, PPh$_3$, P(o-Tol)$_3$ or 1,1'-bis(diphenylphosphino)ferrocene)) and a suitable base (e.g. sodium hydroxide, sodium carbonate, potassium carbonate, cesium carbonate, triethylamine or di-iso-propylamine)), as well as a suitable solvent system (e.g. toluene, ethanol, dimethoxymethane, dimethylformamide, ethylene glycol dimethyl ether, water, dioxane or mixtures thereof). This reaction may be carried out at above room temperature (e.g. at the reflux temperature of the solvent system that is employed). If a protected version of a compound of formula XV is employed, this reaction may be followed by deprotection of the SO$_2$NH-group under standard conditions, for example as described hereinafter.

Compounds of formula II may alternatively be prepared by reaction of a compound of formula XVII,

wherein $X_1$, $X_2$, $X_3$ and $X_4$ are as hereinbefore defined with a compound of formula XVIII,

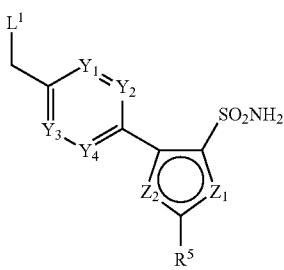

XVIII wherein $Y_1, Y_2, Y_3, Y_4, Z_1, Z_2, R^5$ and $L^1$ are as hereinbefore defined ($L^1$, in particular, may represent bromo), or a N-protected derivative thereof, for example at around or below room temperature in the presence of a suitable base (e.g. potassium hydroxide) and an appropriate organic solvent (e.g. DMSO). If a protected version of a compound of formula XVIII is employed, this reaction may be followed by deprotection of the $SO_2NH$-group under standard conditions, for example as described hereinafter. Additionally, compounds of formula II in which $Z_1$ is —CH=CH— and $Z_2$ is —CH— may be prepared in this way, for example according, or analogously, to processes described in inter alia U.S. Pat. No. 5,312,820. Further, compounds of formula II in which $Z_1$ is —S— and $Z_2$ is —CH— may be prepared in this way for example according, or analogously, to processes described in inter alia UK patent application GB 2281298.

Compounds of formula V may be prepared by oxidation of a compound of formula XIX,

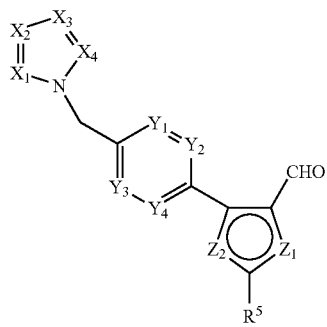

XIX wherein $X_1, X_2, X_3, X_4, Y_1, Y_2, Y_3, Y_4, Z_1, Z_2$ and $R^5$ are as hereinbefore defined, for example under standard oxidation conditions in the presence of a suitable oxidising agent, such as potassium permanganate or chromium (VI) oxide.

Compounds of formulae VII and IX may be prepared by reaction of a compound of formula XVI as hereinbefore defined with (in the case of a compound of formula VII) a compound of formula XX,

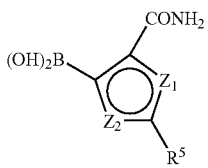

XX or (in the case of a compound of formula IX) a compound of formula XX,

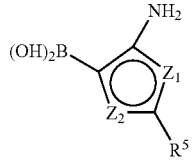

XXI wherein, in both cases, $Z_1$, $Z_2$ and $R^5$ are as hereinbefore defined, or N-protected derivatives thereof, for example under similar conditions to those described hereinbefore for preparation of compounds of formula II (first process). If protected versions of compounds of formulae XX and XXI are employed, these reactions may be followed by deprotection of the NH-group under standard conditions (e.g. acid hydrolysis).

Compounds of formula XVI may be prepared by standard techniques, for example by way of reaction of a compound of formula XVII as hereinbefore defined with a compound of formula XXI,

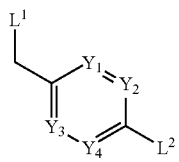

XXII wherein $Y_1, Y_2, Y_3, Y_4, L^1$ and $L^2$ are as hereinbefore defined, for example under similar conditions to those described hereinbefore in respect of preparation of compounds of formula II (second process).

Compounds of formula XVIII are known in the art. For example, they may be prepared according, or analogously, to processes described in inter alia U.S. Pat. No. 5,312,820, UK patent application GB 2281298, and/or by reaction of a compound of formula XV as hereinbefore defined with a compound of formula XXIII,

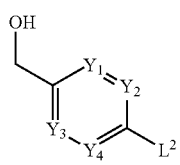

XXIII wherein $Y_1, Y_2, Y_3, Y_4$ and $L^2$ are as hereinbefore defined, for example under similar conditions to those described hereinbefore in respect of preparation of compounds of formula II (first process), followed by conversion of the OH group in the resultant intermediate to an appropriate leaving group, $L^1$ (e.g., in the case where $L^1$ is bromo, conversion may be carried out by reaction with $CBr_4$, for example at or around room temperature in the presence of a base (e.g. triphenylphosphine) and a suitable organic solvent (e.g. DMF)).

Compounds of formula XIX may be prepared by reaction of a compound of formula XVI as hereinbefore defined with a compound of formula XXIV,

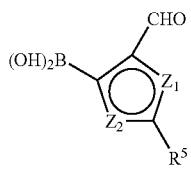

XXIV wherein $Z_1$, $Z_2$ and $R^5$ are as hereinbefore defined, or a protected (at the aldehyde part) derivative thereof, for example under similar conditions to those described hereinbefore for preparation of compounds of formula II (first process). If a protected version of a compound of formula XXIV is employed, this reaction may be followed by deprotection of the CHO-group under standard conditions (e.g. acid hydrolysis).

Compounds of formulae XV, XX, XXI and XXIV and protected derivatives thereof may be prepared by reaction of a corresponding compound of formula XXV,

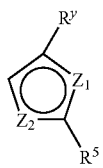

XXV wherein $R^y$ represents $—S(O)_2NH_2$, $—C(O)NH_2$, $—NH_2$ or $—CHO$ (as appropriate) and $R^5$, $Z_1$ and $Z_2$ are as hereinbefore defined, or an appropriate protected derivative thereof, with a reagent system that will enable the introduction of the $—B(OH)_2$ into the appropriate ring system. Suitable reagent systems include trialkylborates (e.g. tri-iso-propylborate). Such reactions may be carried out, for example, at low temperature (e.g. between $-100°$ C. and $0°$ C., e.g. between $-80°$ C. (such as $-78°$ C.) and $-10°$ C. (such as $-20°$ C.)) in the presence of a suitable base (e.g. n-butyl lithium) and an appropriate organic solvent (e.g. THF), followed by acid hydrolysis (e.g. in the presence of dilute HCl).

Compounds of formula XXV are available using known techniques. For example:

(a) Compounds of formula XXV in which $R^y$ represents $—S(O)_2NH_2$, $—C(O)NH_2$ or $—CHO$, and protected derivatives thereof, may be prepared by reaction of a compound of formula XXVI,

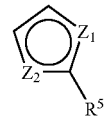

XXVI wherein $R^{ya}$ represents $S(O)_2NH_2$, $—C(O)NH_2$ or $—CHO$ and $Z_1$ and $Z_2$ are as hereinbefore defined, or a protected derivative thereof, with a compound of formula XXVII, $R^5L^3$ XXVII wherein $L^3$ represents a suitable leaving group (such as toluenesulphonate, benzenesulphonate, methanesulphonate or halo, such as bromo or iodo) and $R^5$ is as hereinbefore defined, for example at below room temperature (e.g. between around $-35°$ C. and around $-85°$ C.), in the presence of a suitable base (e.g. n-butyl lithium) and an appropriate solvent (e.g. THF).

(b) Compounds of formula XXV in which $R^y$ is $—S(O)_2NH_2$ and N-protected derivatives thereof, may be prepared by reaction of an appropriate compound of formula XXVIII,

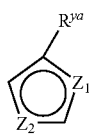

XXVIII wherein $R^5$, $Z_1$ and $Z_2$ are as hereinbefore defined with an appropriate reagent for introduction of a $—S(O)_2NH_2$ group into the appropriate ring system (for example chlorosulphonic acid, or thionyl chloride in the presence of a suitable strong base (e.g. butyl lithium)), followed by reaction of the resultant intermediate with ammonia, or a protected derivative thereof (e.g. tert-butylamine), under conditions that are well known to those skilled in the art.

(c) Certain protected derivatives (e.g. alkyl, such as $C_{1-6}$ alkyl, for example tert-butyl, protected derivatives) of compounds of formula V in which $R^y$ represents $—C(O)NH_2$ may be prepared by reaction of a compound of formula XXVIII as hereinbefore defined, with a compound of formula XXIX, $R^zN{=}C{=}O$ XXIX wherein $R^z$ represents an appropriate protecting group, such as an alkyl group, including $C_{1-6}$ alkyl, e.g. tert-butyl, for example at low temperature (e.g. $-78°$ C. to around $0°$ C.), in the presence of a suitable base (e.g. n-butyl lithium) and an appropriate solvent (e.g. THF).

(d) Certain protected derivatives (e.g. alkyl, such as $C_{1-6}$ alkyl, for example tert-butyl, protected derivatives) of compounds of formula XXV in which $R^y$ represents $—C(O)NH_2$ may also be prepared by reaction of a compound of formula XXX,

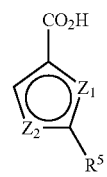

XXX wherein $R^5$, $Z_1$ and $Z_2$ are as hereinbefore defined with a protected (e.g. an (e.g. $C_{1-6}$) alkyl, such as tert-butyl-protected) derivative of ammonia (e.g. tert-butylamine) under standard coupling conditions (see, for example, those described hereinbefore for preparation of compounds of formula I (process step (iii))). Compounds of formula XXX are known in the art or may be prepared by way of standard techniques, for example oxidation of a corresponding compound of formula XXV in which $R^y$ is $—CHO$ e.g. under those conditions described hereinbefore for preparation of compounds of formula V.

(e) Compounds of formula XXV in which $R^y$ is $—CHO$, $Z_1$ represents $—CH{=}CH—$ and $Z_2$ represents $—CH—$, and protected derivatives thereof, may be prepared by reaction of a compound of formula XXVIII in which $Z_1$ represents $—CH{=}CH—$ and $Z_2$ represents $—CH—$ with an appropriate reagent system for the introduction of an aldehyde group into the benzene ring (e.g. TiCl$_4$/CHCl$_3$, SnCl$_4$/CH$_2$Cl$_2$ or 1,3,5,7-azaadamantane/TFA) under standard reaction conditions, followed by (if appropriate) protection of the resultant benzaldehyde under standard conditions.

(f) Compounds of formula XXV in which R$^y$ is —NH$_2$, Z$_1$ represents —CH=CH— and Z$_2$ represents —CH—, and N-protected derivatives thereof, may be prepared by nitration of a compound of formula XXVIII in which Z$_1$ represents —CH=CH— and Z$_2$ represents —CH—, followed by reduction of the resultant nitrobenzene and (if appropriate) protection of the resultant aminobenzene, all of which steps may be carried out under standard conditions.

Compounds of formulae III, IV, VI, VIII, X, XI, XII, XIII, XIV, XVII, XXII, XXIII, XXVI, XXVII, XII and XXIX are either commercially available, are known in the literature, or may be obtained either by analogy with the processes described herein, or by conventional synthetic procedures, in accordance with standard techniques, from readily available starting materials using appropriate reagents and reaction conditions.

Compounds of the invention may be isolated from their reaction mixtures using conventional techniques.

It will be appreciated by those skilled in the art that, in the processes described above and hereinafter, the functional groups of intermediate compounds may need to be protected by protecting groups.

Functional groups that it is desirable to protect include sulphonamido, amido, amino and aldehyde. Suitable protecting groups for sulphonamido, amido and amino include tert-butyloxycarbonyl, benzyloxycarbonyl, 2-trimethylsilylethoxycarbonyl (Teoc) or tert-butyl. Suitable protecting groups for aldehyde include alcohols, such as methanol or ethanol, and diols, such as 1,3-propanediol or, preferably, 1,2-ethanediol (so forming a cyclic acetal).

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques (e.g. using trifluoroacetic acid, sulfuric acid, toluenesulfonic acid or boron trichloride).

Persons skilled in the art will appreciate that, in order to obtain compounds of the invention in an alternative, and, on some occasions, more convenient, manner, the individual process steps mentioned hereinbefore may be performed in a different order, and/or the individual reactions may be performed at a different stage in the overall route (i.e. substituents may be added to and/or chemical tansformations performed upon, different intermediates to those mentioned hereinbefore in conjunction with a particular reaction). This may negate, or render necessary, the need for protecting groups.

The type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", 3$^{rd}$ edition, T. W. Greene & P. G. M. Wutz, Wiley-Interscience (1999).

Medical and Pharmaceutical Uses

Compounds of the invention are useful because they possess pharmacological activity. The compounds of the invention are therefore indicated as pharmaceuticals.

According to a further aspect of the invention there is thus provided the compounds of the invention for use as pharmaceuticals.

In particular, compounds of the invention are agonists of AngII, more particularly, are agonists of the AT2 receptor, and, especially, are selective agonists of that sub-receptor, for example as may be demonstrated in the tests described below. The compounds of the invention are thus expected to be useful in those conditions in which endogenous production of AngII is deficient and/or where an increase in the effect of AngII is desired or required.

The compounds of the invention are further expected to be useful in those conditions where AT2 receptors are expressed and their stimulation is desired or required.

The compounds of the invention are further indicated in the treatment of conditions characterised by vasoconstriction, increased cell growth and/or differentiation, increased cardiac contractility, increased cardiovascular hypertrophy, and/or increased fluid and electrolyte retention.

The compounds of the invention are further indicated in the treatment of stress-related disorders, and/or in the improvement of microcirculation and/or mucosa-protective mechanisms.

Thus, compounds of the invention are expected to be useful in the treatment of disorders, which may be characterised as indicated above, and which are of, for example, the gastrointestinal tract, the cardiovascular system, the respiratory tract, the kidneys, the eyes, the female reproductive (ovulation) system and the central nervous system (CNS).

Disorders of the gastrointestinal tract that may be mentioned include oesopbagitis, Barrett's oesophagus, gastric ulcers, duodenal ulcers, dyspepsia (including non-ulcer dyspepsia), gastro-oesophageal reflux, irritable bowel syndrome (IBS), inflammatory bowel disease (IBD), pancreatitis, hepatic disorders (such as hepatitis), gall bladder disease, multiple organ failure (MOF) and sepsis. Other gastrointestinal disorders that may be mentioned include xerostomia, gastritis, gastroparesis, hyperacidity, disorders of the bilary tract, coelicia, Crohn's disease, ulcerative colitis, diarrhoea, constipation, colic, dysphagia, vomiting, nausea, indigestion and Sjögren's syndrome.

Disorders of the respiratory tract that may be mentioned include inflammatory disorders, such as asthma, obstructive lung diseases (such as chronic obstructive lung disease), pneumonitis, pulmonary hypertension and adult respiratory distress syndrome.

Disorders of the kidneys that may be mentioned include renal failure, nephritis and renal hypertension.

Disorders of the eyes that may be mentioned include diabetic retinopathy, premature retinopathy and retinal microvascularisation.

Disorders of the female reproductive system that may be mentioned include ovulatory dysfunction.

Cardiovascular disorders that may be mentioned include hypertension, cardiac hypertrophy, cardiac failure, artherosclerosis, arterial thrombosis, venous thrombosis, endothelial dysfunction, endothelial lesions, post-balloon dilatation stenosis, angiogenesis, diabetic complications, microvascular dysfunction, angina, cardiac arrhythmias, claudicatio intermittens, preeclampsia, myocardial infarction, reinfarction, ischaemic lesions, erectile dysfunction and neointima proliferation.

Disorders of the CNS that may be mentioned include cognitive dysfunctions, dysfunctions of food intake (hunger/satiety) and thirst, stroke, cerebral bleeding, cerebral embolus and cerebral infarction.

Compounds of the invention may also be useful in the modulation of growth metabolism and proliferation, for example in the treatment of hypertrophic disorders, prostate hyperplasia, autoimmune disorders, psoriasis, obesity, neuronal regeneration, the healing of ulcers, inhibition of adipose tissue hyperplasia, stem cell differentiation and proliferation, cancer (e.g. in the gastrointestinal tract, lung cancer, etc), apoptosis, tumours (generally) and hypertrophy, diabetes, neuronal lesions and organ rejection.

The compounds of the invention are indicated both in the therapeutic and/or prophylactic treatment of the above conditions.

According to a further aspect of the present invention, there is provided a method of treatment of a condition in which endogenous production of AngII is deficient, and/or a condition where an increase in the effect of AngII is desired or required, and/or a condition where AT2 receptors are expressed and their stimulation is desired or required, which method comprises administration of a therapeutically effective amount of a compound of the invention to a person suffering from, or susceptible to, such a condition.

The compounds of the invention will normally be administered orally, intravenously, subcutaneously, buccally, rectally, dermally, nasally, tracheally, bronchially, by any other parenteral route or via inhalation, in a pharmaceutically acceptable dosage form.

When the condition to be treated is multiple organ failure, preferred routes of administration are parenteral (e.g. by injection). Otherwise, the preferred route of administration for compounds of the invention is oral.

The compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like.

Such formulations may be prepared in accordance with standard and/or accepted pharmaceutical practice.

According to a further aspect of the invention there is thus provided a pharmaceutical formulation including a compound of the invention, in admixture with a pharmaceutically acceptable adjuvant, diluent or carrier.

Compounds of the invention may also be administered in combination with other AT2 agonists that are known in the art, as well as in combination with AT1 receptor antagonists that are known in the art, such as losartan, or in combination with an inhibitor of angiotensin converting enzyme (ACE).

According to a further aspect of the invention, there is provided a combination product comprising:
(A) a compound of the invention; and
(B) an AT1 receptor antagonist, or an ACE inhibitor,
wherein each of components (A) and (B) is formulated in admixture with a pharmaceutically-acceptable adjuvant, diluent or carrier.

Such combination products provide for the administration of compound of the invention in conjunction with an AT1 receptor antagonist, or an ACE inhibitor, and may thus be presented either as separate formulations, wherein at least one of those formulations comprises compound of the invention, and at least one comprises AT1 receptor antagonist, or ACE inhibitor, or may be presented (i.e. formulated) as a combined preparation (i.e. presented as a single formulation including compound of the invention and AT1 receptor antagonist or ACE inhibitor).

Thus, there is further provided:
(1) a pharmaceutical formulation including a compound of the invention and an AT1 receptor antagonist, or an ACE inhibitor, in admixture with a pharmaceutically-acceptable adjuvant, diluent or carrier; and
(2) a kit of parts comprising components:
(a) a pharmaceutical formulation including a compound of the invention, in admixture with a pharmaceutically-acceptable adjuvant, diluent or carrier; and
(b) a pharmaceutical formulation including an AT1 receptor antagonist, or an ACE inhibitor, in admixture with a pharmaceutically-acceptable adjuvant, diluent or carrier,
which components (a) and (b) are each provided in a form that is suitable for administration in conjunction with the other.

Depending upon the disorder and patient to be treated and the route of administration, the compounds of the invention may be administered at varying doses.

Although doses will vary from patient to patient, suitable daily doses are in the range of about 1 to 1000 mg per patient, administered in single or multiple doses. More preferred daily doses are in the range 2.5 to 250 mg per patient.

Individual doses of compounds of the invention may be in the range 1 to 100 mg.

In any event, the physician, or the skilled person, will be able to determine the actual dosage which will be most suitable for an individual patient, which is likely to vary with the condition that is to be treated, as well as the age, weight, sex and response of the particular patient to be treated. The above-mentioned dosages are exemplary of the average case; there can, of course, be individual instances where higher or lower dosage ranges are merited, and such are within the scope of this invention.

Compounds of the invention have the advantage that they bind selectively to, and exhibit agonist activity at, the AT2 receptor. By compounds which "bind selectively" to the AT2 receptor, we include that the affinity ratio for the relevant compound (AT2:AT1) is at least 5:1, preferably at least 10:1 and more preferably at least 20:1.

The compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art.

Biological Tests

The following test procedures may be employed.

Test A

Receptor Binding Assay using Rat Liver Membrane $AT_1$ Receptor

Rat liver membranes were prepared according to the method of Dudley et al (*Mol. Pharmacol.* (1990) 38, 370). Binding of [$^{125}$I]Ang II to membranes was conducted in a final volume of 0.5 mL containing 50 mM Tris-HCl (pH 7.4), 100 mM NaCl, 10 mM $MgCl_2$, 1 mM EDTA, 0.025% bacitracin, 0.2% BSA (bovine serum albumin), liver homogenate corresponding to 5 mg of the original tissue weight, [$^{125}$I]Ang II (70 000 cpm, 0.03 nM and variable concentrations of test substance. Samples were incubated at 25° C. for 1 h, and binding was terminated by filtration through Whatman GF/B glass-fiber filter sheets using a Brandel cell harvester. The filters were washed with 4×2 mL of Tris-HCl (pH 7.4) and transferred to tubes. The radioactivity was measured in a gamma counter. The characteristics of the Ang II binding $AT_1$ receptor were determined by using six different concentrations (0.03-5 mmol/L) of the labeled [$^{125}$I]AngII. Non-specific binding was determined in the presence of 1 μM Ang II. The specific binding was determined by subtracting the non-specific binding from the total bound [$^{125}$I]AngII. The dissociation constant ($K_d$=1.7±0.1 nM, [L]=0.057 nM) was determined by Scatchard analysis of data obtained with Ang II by using GraFit (Erithacus Software, UK). The binding data were best fitted with a one-site fit. All experiments were performed at least in triplicate.

Test B

Receptor Binding Assay using Porcine Myometrial Membrane $AT_2$ Receptor

Myometrial membranes were prepared from porcine uteri according to the lo method by Nielsen et al (*Clin. Exp. Pharm. Phys.* (1997) 24, 309). Any possible interference that may be exhibited by binding of compound to $AT_1$ receptors was blocked by addition of 1 μM of a selective AT1 inhibitor. Binding of [$^{125}$I]Ang II to membranes was conducted in a final volume of 0.5 mL containing 50 mM Tris-HCl (pH 7.4), 100 mM NaCl, 10 mM $MgCl_2$, 1 mM EDTA, 0.025% bacitracin, 0.2% BSA, homogenate corresponding to 10 mg of the original tissue weight, [$^{125}$I]Ang II (70 000 cpm, 0.03 nM) and variable concentrations of test substance. Samples were incubated at 25° C. for 1 h, and binding was terminated by filtration through Whatman GF/B glass-fiber filter sheets using a Brandel cell harvester. The filters were washed with 3×3 mL of Tris-HCl (pH 7.4) and transferred to tubes. The radioactivity was measured using a gamma counter. The characteristics of the Ang II binding $AT_2$ receptor was determined by using six different concentrations (0.03-5 mmol/L) of the labeled [$^{125}$I]Ang II. Non-specific binding was determined in the presence of 1 μM Ang II. The specific binding was determined by subtracting the non-specific binding from the total bound [$^{125}$I]Ang II. The dissociation constant ($K_d$=0.7±0.1 nM, [L]=0.057 nM) was determined by Scatchard analysis of data obtained with Ang II by using GraFit (Erithacus Software, UK). The binding data were best fitted with a one-site fit. All experiments were performed at least in triplicate.

Test C

Duodenal Mucosal Alkaline Secretion Assay

Compounds were exposed to the duodenal mucosa in barbiturate-anaesthetised rats prepared for in situ titration of duodenal mucosal alkaline secretion, according to the methodology described by Flemström et al in *Am. J. Physiol.* (1982) 243, G348.

The invention is illustrated by way of the following examples.

EXAMPLE 1

N-Butyloxycarbonyl-3-(4-imidazol-1-ylmethylphenyl)-5-iso-butylthiophene-2-sulfonamide (a) N-tert-Butylthiophene-2-sulfonamide Thiophene-2-sulfonyl chloride (15 g, 0.082 mol) was dissolved in $CHCl_3$ (200 mL) under $N_2$ atmosphere and then cooled to 0° C. tert-Butylamine (25.9 mL, 0.246 mol) dissolved in $CHCl_3$ (50 mL) was then added dropwise to the reaction mixture. The reaction mixture was stirred for 1 h at room temperature and then at reflux for 10 min. Toluene (700 mL) was added and the organic phase was washed with water (3×50 mL), dried, and concentrated in vacuo. The sub-title product was used without further purification in the next step.

$^1$H NMR δ($CDCl_3$): 7.60(1H, dd, J=1.3, 3.8 Hz), 7.53(1H, dd, J=1.3, 5.0 Hz), 7.02(1H, dd, J=5.0, 3.8 Hz), 5.13(1H, m), 1.24 (9H, m)

$^{13}$C NMR δ($CDCl_3$): 145.0, 131.7, 131.2, 127.0, 55.1, 29.9

(b) 5-iso-Butyl-N-tert-butylthiophene-2-sulfonamide

N-tert-Butylthiophene-2-sulfonamide (10 g, 0.046 mol, see step (a) above) was dissolved in THF (85 mL) under $N_2$ and then cooled to −78° C. n-BuLi (1.6 M, 76.9 mL, 0.12 mol) was added via a syringe. The reaction mixture was stirred at −78° C. for 30 min. and then at −40° C. for 2 h. Iodo-2-methylpropane (10.5 mL, 0.09 mol) was added dropwise to the reaction mixture. The reaction mixture was stirred overnight at room temperature. The reaction was quenched with $NH_4Cl$ (aq.) and extracted with EtOAc. The combined organic phase was washed with brine and dried and concentrated in vacuo. The crude product was purified on column chromatography (hexanes:EtOAc (10:1)) to give the sub-title compound in 55% yield (7.0 g, 0.025 mol).

$^1$H NMR δ($CDCl_3$): 7.43(1H, d, J=3.6 Hz), 6.67(1H, d, J=3.8 Hz), 4.83(1H, m), 2.67(2H, d, J=7 Hz), 1.88 (1H, m), 1.26(9H, m), 0.93(6H, J=6.6 Hz).

$^{13}$C NMR B($CDCl_3$): 145.0, 131.7, 131.2, 127.0, 55.1, 29.9

(c) 5-iso-Butyl-2-(N-tert-butylaminosulfonyl)thiophene-3-boronic acid 5-iso-Butyl-N-tert-butylthiophene-2-sulfonamide (10.6 g, 0.039 mol, see step (b)) above) was dissolved in THF (165 mL) under $N_2$ and then cooled to −78° C. n-BuLi (1.6 M, 60.19 mL, 0.096 mol) was added via a syringe. The reaction mixture was stirred at −20° C. for 4 h. The tri-iso-propylborate (13.3 mL, 0.058 mol) was then added via a syringe and the reaction mixture was stirred overnight at room temperature. The reaction was quenched with 2 M HCl (20 mL). The organic phase was separated and the water phase was extracted with EtOAc (3×100 mL). The combined organic phase was washed with brine, dried and concentrated in vacuo. The product was used without further purification.

MS($ESI^+$) m/z: 236.8

(d) 1-(4Bromobenzyl)-1H-imidazole

Dimethyl sulphoxide (20 mL; dried over 4 A molecular sieve) was added to potassium hydroxide (2.24 g, 0.04 mol, crushed pellets) and the mixture was stirred for 5 min. Imidazole (0.5718 g, 0.0084 mol) was then added and the mixture was stirred for 2 h. 4-Bromobenzyl bromide (3.25 g, 0.013 mol) was added and the mixture was cooled briefly and stirred for a further 1 h before water (20 mL) was added. The mixture was extracted with ether (3×100 mL) and each extract was washed with water (3×50 mL). The combined ether layers were dried over $CaCl_2$ and the solvent was removed in vacuo. The residue was chromatographed on silica gel with $CHCl_3$:MeOH (30:1) plus 0.05% formic acid as eluent to give the sub-title product (1.275 g, yield: 53%).

$^1$H NMR δ($CDCl_3$): 7.73(3H, m), 7.28(3H, m), 7.15(1H, m), 5.30(2H, s)

$^{13}$C NMR δ($CDCl_3$): 136.8, 134.8, 131.5, 129.3, 128.4, 121.5, 118.7, 49.4.

MS($ESI^+$) m/z: 236.8

(e) 3-(4-Imidazol-1-ylmethylphenyl)-5-iso-butyl-N-tert-butylthiophene-2-sulfonamide 5-iso-Butyl-2-(N-tert-butylaminosulfonyl)thiophene-3-boronic acid (200.5 mg, 0.628 mmol, see step (c) above), 1-(4-bromobenzyl)-1H-imidazole (98.8 mg, 0.416 mmol, see step (d) above), toluene (15 mL), ethanol (15 mL), NaOH (1.0M, 1.5 mL, 1.5 mmol) and Pd(PPh$_3$)$_4$ (14.5 mg, 0.125 mmol) were mixed under N$_2$. The mixture was warmed to reflux for 2 h. The mixture was diluted with EtOAc (50 mL), washed with water and brine, and dried over MgSO$_4$. The solvent was removed and the residue was separated by column chromatography with chloroform:methanol (20:1) as an eluent to give 113.9 mg of the sub-title compound (yield: 63.27%).

IR(neat): 3060, 2996, 1507 cm$^{-1}$ $^1$H NMR δ(CDCl$_3$): 7.39(1H,s), 7.35(2H, d, J=8.1 Hz), 6.98(2H, d, J=8.1 Hz), 6.96(1H, s), 6.84(H, s), 6.47(H, s), 4.91(2H, s), 3.96(1H,s), 2.72(H, brs), 2.42(2H, d, J=7.1 Hz), 1.64(1H, m), 0.73(9H, s), 0.72(6H, d, J=6.9 Hz)

$^{13}$C NMR δ(CDCl$_3$): 148.6, 142.3, 137.2, 136.2, 135.1, 129.7, 129.4, 128.8, 127.4, 119.2, 54.6, 50.6, 39.2, 30.5, 29.5, 22.1

MS(ESI$^+$) m/z: 431.9 Anal. Calcd. for C$_{22}$H$_{29}$N$_3$O$_2$S$_2$: C, 58.8; H. 7.0; N, 9.4. Found: C, 58.7.0; H, 6.7; N, 9.1.

(f) 3-(4-Imidazol-1-ylmethylphenyl)-5-iso-butylthiophene-2-sulfonamide

Trifluoroacetic acid was added (2 mL) to 3-(4-imidazol-1-ylmethylphenyl)-5-iso-butyl-N-tert-butylthiophene-2-sulfonamide (113 mg, 0.2618 mmol, see step (e) above) and one drop (ca. 0.05 mL) of anisole (ca. 0.05 mL) was added to the mixture. The reaction mixture was stirred under N$_2$ atmosphere for 30 h and then evaporated and co-evaporated with acetonitrile until TLC showed that it was pure. The crude product was used directly in the next step without further purification.

$^1$H NMR δ(CDCl$_3$): 7.70(1H,s), 7.57(2H, d, J=8.1 Hz), 7.19(2H, d, J=8.1 Hz), 7.10(1H, s), 6.93(H, s), 6.73(H, s), 5.14(2H, s), 2.67(2H, d, J=7.1 Hz), 2.62(H, brs), 1.94(1H, m), 0.97(6H, d, J=6.6 Hz)

$^{13}$C NMR δ(CDCl$_3$): 148.4, 142.9, 137.2, 136.2, 134.6, 129.7, 129.3, 128.8, 127.3, 119.2, 50.6, 39.2, 30.5 22.1

MS(EI$^+$) m/z: 375.9

(g) N-Butyloxycarbonyl-3-(4-imidazol-1-ylmethylphenyl)-5-iso-butylthiophene-2-sulfonamide The crude 3-(4-imidazol- 1 -ylmethylphenyl)-5-iso-butylthiophene-2-sulfonamide from step (f) above was dissolved in pyridine (2 mL, dried over 4 Å molecular sieve). Pyrrolidinopyridine (40.52 mg, 0.2618 mmol) and butyl chloroformate (363.5 mg, 0.339 mL) were added to the mixture. The mixture was stirred overnight under a N$_2$ atmosphere at room temperature. Evaporation and co-evaporation with acetonitrile to remove the solvents and purification on column chromatography with 10% MeOH in chloroform as eluent gave the title compound (57.8 mg, 0.1217 mmol) in a 46.5% yield (over the last two steps).

IR(neat): 3555.8, 3120.3, 2955.9, 1694.2, 1268.5 cm$^{-1}$ $^1$H NMR δ(CDCl$_3$): 7.96(1H,s), 7.57(2H, d, J=7.9 Hz), 7.10(2H, d, J=7.9 Hz), 6.89(H, s), 6.85(H, s), 6.74(H, s), 5.16(2H, s), 4.03(2H, t, J=6.6 Hz), 2.71(2H, d, J=7.1 Hz), 1.94(1H, m), 1.51(2H,m), 1.25(2H, m), 0.98(6H, d, J=6.6 Hz), 0.87(3H, t, J=7.4 Hz)

$^{13}$C NMR δ(CDCl$_3$): 152.5, 158.4, 143.9, 136.4, 134.6, 133.0, 129.8, 128.9, 127.3, 125.6, 119.6, 65.9, 51.2, 39.3, 30.6, 30.4, 22.3, 18.9, 13.7

MS(EI$^+$) m/z: 476.0 Anal. Calcd for C$_{23}$H$_{29}$N$_3$O$_4$S$_2$H$_2$O: C, 56.0; H, 6.3; N, 8.5. Found: C, 56.4; H, 6.2; N, 8.6

EXAMPLE 2

N-iso-Butyloxycarbonyl-3-(4imidazol-1-ylmethylphenyl)-5-iso-butyl-thiophene-2-sulfonamide 30 mg of crude 3(4-imidazol-1-ylmethylphenyl)5-iso-butylthiophene-2-sulfonamide (see Example 1(f) above) was dissolved in pyridine (1 mL, dried over 4 Å molecular sieve) and cooled on ice. Pyrrolidinopyridine (11.8 mg, 0.080 mmol) and iso-butyl chloroformate (103.6 μL, 0.80 mmol) were then added to the mixture. The mixture was stirred overnight under a N$_2$ atmosphere at 50° C. Evaporation and co-evaporation with acetonitrile to remove the solvents, followed by purification by column chromatography using 10% MeOH in CHCl$_3$ as eluent gave the title compound (27 mg, 0.057 mmol) in 71% yield.

$^1$H NMR δ(CD$_3$OD): 8.18 (brs, 1H), 7.58 (d, J=7.9 Hz, 2H), 7.32 (d, J=7.9 Hz, 2H), 7.29 (brs, 1H), 7.17 (brs, 1H), 6.82 (s, 1H), 5.30 (s, 2H), 3.70 (d, J=6.6 Hz, 2H), 2.72 (d, J=7.1 Hz, 2H), 1.93 (m, 1H), 1.76 (m, 1H), 0.99 (d, J=6.6 Hz, 6H), 0.81 (d, J=7.4 Hz, 6H)

$^{13}$C NMR δ(CD$_3$OD): 155.7, 150.5, 145.2, 137.0, 136.4, 135.6, 131.0, 130.5, 128.9, 126.6, 121.8, 73.0, 52.2, 40.0, 31.9, 29.1, 22.6, 19.3

MS (ESI$^+$) m/z: 476.0

EXAMPLE 3

N-iso-Propyloxycarbonyl-3-(4-imidazol-1-ylmethylphenyl)-5-iso-butyl-thiophene-2-sulfonamide 100 mg of crude 3-(4-imidazol-1-ylmethylphenyl)-5-isobutylthiophene-2-sulfonamide (see Example 1(f) above) was dissolved in pyridine (4 mL, dried over 4 Å molecular sieve) and cooled on ice. Pyrrolidinopyridine (39.5 mg, 0.266 mmol) and iso-propyl chloroformate (1M in toluene, 2.66 mL, 2.66 mmol) were then added to the mixture. The mixture was stirred overnight under N$_2$ atmosphere at 50° C. Evaporation and co-evaporation with acetonitrile to remove the solvents, followed by purification using preparative LC/MS (30% acetonitrile to pure acetonitrile, reverse phase) gave the title compound (52.6 mg, 0.114 mmol).

$^1$H NMR δ(CD$_3$OD): 8.16 (brs, 1H), 7.58 (d, J=8.1 Hz, 2H), 7.34 (d, J=8.1 Hz, 2H), 7.32 (s, 1H), 7.18 (s, 1H), 6.84 (s, 1H), 5.32 (s, 2H), 4.72 (sep, J=6.3 Hz, 1H), 2.73 (d, J=7.1 Hz, 2H), 1.94 (m, 1H), 1.09 (d, J=6.3 Hz, 6H), 1.00 (d, J=6.6 Hz, 6H)

$^{13}$C NMR δ(CD$_3$OD): 155.5, 151.0, 145.6, 137.2, 136.2, 135.0, 131.0, 130.5, 128.9, 126.8, 122.0, 70.5, 52.1, 40.0, 31.9, 22.6, 22.1

MS (ESI$^+$) m/z: 462.0

EXAMPLE 4

N-(Butoxyacetyl)-3-(4-imidazol-1-ylmethylphenyl)-5-iso-butylthiophene-2-sulfonamide CDI (1,1'-carbonyl-diimidazole, 129.5 mg, 0.80 mmol) was added to a solution of butoxyacetic acid (103.8 μL, 0.80 mmol) in dry THF (4 mL). The mixture was stirred at 50° C. for 2.5 h. A solution of 3-(4-imidazol-1-ylmethylphenyl)-5-iso-butylthiophene-2-sulfonamide (see Example 1(f) above; 100 mg) and DBU (1,8-diazabicyclo[5.4.0]undec-7-ene, 19.9 μL, 0.133 mmol) in dry THF (4 mL) was added to the reaction mixture. The reaction mixture was then stirred overnight at 50° C. MeOH (20 mL) was added to the reaction mixture, which was then concentrated in vacuo. The residue was dissolved in EtOAc (100 mL) and then washed with water (3×50 mL). The organic phase was dried and evaporated. The crude product was purified by column chromatography using 10% MeOH in CHCl$_3$ as eluent to give the title compound (27 mg, 0.057 mmol).

$^1$H NMR δ(CD$_3$OD): 7.96 (brs, 1H), 7.66 (d, J=8.3 Hz, 2H), 7.30 (d, J=8.3 Hz, 2H), 7.21 (brs, 1H), 7.07 (brs, 1H), 6.79 (s, 1H), 5.26 (s, 2H,), 3.67 (s, 2H,), 3.40 (t, J=6.8 Hz, 2H), 2.66 (d, J=6.9 Hz, 2H), 1.88 (m, 1H), 1.48 (m, 2H), 1.29 (m, 4H), 0.96 (d, J=6.6 Hz, 6H), 0.82 (t, J=7.3 Hz, 3H)

$^{13}$C NMR δ(CD$_3$OD): 178.3, 148.3, 143.4, 138.0, 137.3, 136.6, 131.1, 130.3, 128.5, 128.2, 127.6, 121.4, 72.4, 72.3, 51.7, 39.9, 32.2, 31.8, 30.7, 22.6, 20.1, 14.3

MS (ESI$^+$) m/z: 490.1

EXAMPLE 5

N-Butyloxycarbonyl-3-(4imidazol-1-ylmethylphenyl)-5-butylthiophene-2-sulfonamide (a) 5-Butylthiophene-2-sulfonic acid tert-butylamide N-tert-Butylthiophene-2-sulfonamide (5 g, 0.0228 mol, see Example 1(a) above) was dissolved in THF (43 mL) under N$_2$ and then cooled to −78° C. n-BuLi (1.6 M, 38.5 mL, 0.062 mol) was added via a syringe. The reaction mixture was stirred at −78° C. for 30 min and then at −40° C. for 2 h. Iodo-butane (5.19 mL, 0.046 mol) was added dropwise to the reaction mixture. The reaction mixture was stirred overnight at room temperature, quenched with NH$_4$Cl (aq) and extracted with EtOAc. The combined organic phase was washed with brine, dried and concentrated in vacuo. The crude product was purified on column chromatography (Hex: EtOAc 10:1) to give the sub-title compound in 46% yield (2.92 g, 0.011 mol).

$^1$H NMR δ(CDCl$_3$): 7.41 (d, J=3.6 Hz, 1H), 6.69 (d, J=3.8 Hz, 1H), 4.96 (m, 1H), 2.80 (d, J=7.6 Hz, 2H), 1.65 (m, 2H), 1.37 (m, 2H), 1.26 (s, 9H), 0.92 (t, J=7.26 Hz, 3H)

$^{13}$C NMR δ(CDCl$_3$): 153.0, 141.7, 131.9, 124.0, 54.9, 33.4, 29.9, 22.0, 13.6.

(b) 5-Butyl-2-(N-tert:-butylaminosulfonyl)thiophene-3-boronic acid

5-Butylthiophene-2-sulfonic acid tert-butylamide (2.9 g, 0.010 mol, see step (a) above) was dissolved in THF (40 mL) under N$_2$ and then cooled to −78° C. n-BuLi (1.6 M, 16.2 mL, 0.026 mol) was added via a syringe. The reaction mixture was stirred at −20° C. for 4 hours. Tri-iso-propylborate (13.3 mL, 0.058 mol) was then added via a syringe and the reaction mixture was stirred overnight at room temperature. The reaction was quenched with 2 M HCl (20 mL). The organic phase was separated and the water phase was extracted with EtOAc (3×100 mL). The combined organic phase was washed with brine and dried and concentrated in vacuo. The product was used in the next step without fit her purification.

MS (ESI$^+$) m/z: 320.1

(c) 3-(4-Imidazol-1-ylmethylphenyl)-5-butyl-N-tert-butylthiophene-2-sulfonamide

5-Butyl-2-(N-tert-butylaminosulfonyl)thiophene-3-boronic acid (300 mg, 1.27 mmol, see step (b) above), 1-(4-bromobenzyl)-1H-imidazole (606 mg, 1.90 mmol, see Example 1(d) above), toluene (15 mL), ethanol (4 mL), NaOH (1.0 M, 4.0 mL, 5.1 mmol) and Pd(PPh$_3$)$_4$ (43.9 mg, 0.038 mmol) were mixed under N$_2$. The mixture was warmed to reflux for 2 hours, diluted with EtOAc (50 mL), washed with water and brine, and dried over MgSO$_4$. The solvent was removed and the residue was separated by column chromatography using chloroform:methanol (20:1) as eluent. The product was not completely pure but was used in the next step without further purification.

(d) 3-(4-Imidazol-1-ylmethylphenyl)-5-butylthiophene-2-sulfonamide

Trifluoroacetic acid was added (10 mL) to the crude 3-(4imidazol-1-ylmethylphenyl)-5-butyl-N-tert-butylthiophene-2-sulfonamide from step (c) above, and one drop (ca. 0.05 mL) of anisol was added to the mixture. The reaction mixture was stirred under N$_2$ atmosphere for 30 hours and then evaporated and co-evaporated with acetonitrile. The crude product was purified by column chromatography (CH$_2$Cl$_2$:MeOH (20:1)) to give sub-title compound (232 mg, 0.62 mmol) in 49% yield (from 1-(4-bromobenzyl)-1H-imidazole).

$^1$H NMR δ(CDCl$_3$, CD$_3$OD): 8.97(1H,s), 7.64-7.40 (m, 6H), 6.82 (s, 1H), 5.44 (s, 2H), 2.83 (t, J=7.6 Hz, 2H), 1.68 (m, 1H), 1.39 (m, 1H), 0.95 (t, J=7.26 Hz, 1H)

$^{13}$C NMR δ(CDCl$_3$, CD$_3$OD): 150.3, 143.8, 136.9, 136.2, 134.9, 131.1, 129.7, 129.3, 123.1, 121.5, 53.3, 34.4, 30.3, 22.9, 14.0

MS (ESI$^+$) m/z: 376.1

(e) N-Butyloxycarbonyl-3-(4-imidazol-1-ylmethylphenyl)-5-butylthiophene-2-sulfonamide 3-(4Imidazol-1-ylmethylphenyl)-5-butylthiophene-2-sulfonamide (232 mg, 0.62 mmol; see step (d) above) was dissolved in pyridine (3 mL, dried over 4 Å molecular sieves). Pyrrolidinopyridine (91.6 mg, 0.618 mmol) and butyl chloroformate (785.7 μL, 0.618 mmol) were added to the mixture. The mixture was stirred overnight under a N$_2$ atmosphere at room temperature. Evaporation and co-evaporation with acetonitrile to remove the solvents, followed by purification by column chromatography using 10% MeOH in chloroform as eluent, gave the title compound (29 mg, 0.061 mmol) in 10% yield.

$^1$H NMR δ(CD$_3$OD): 7.94 (s, 1H), 7.63 (d, J=8.1 Hz, 2H), 7.28 (d, J=8.1 Hz, 2H), 7.20 (s, 1H), 7.06 (s, 1H), 6.8 (s, 1H), 5.25 (s, 2H), 3.88 (t, J=6.3 Hz, 2H), 2.84 (t, J=7.4 Hz, 2H), 1.68 (m, 1H), 1.44 (m, 4H), 1.26 (m, 2H), 0.96 (t, J=7.3 Hz, 3H), 0.87 (t, J=7.3 Hz, 3H)

$^{13}$C NMR δ(CD$_3$OD): 159.5, 150.2, 143.9, 138.4, 137.2, 136.6, 131.0, 129.5, 128.5, 128.0, 121.4, 66.5, 51.7, 49.0, 34.7, 32.1, 30.5, 23.2, 20.1, 14.1

MS (ESI$^+$) m/z: 476.1

EXAMPLE 6

N-Butyloxycarbonyl-2-(4-imidazol-1-ylmethylphenyl)-4-iso-butylbenzenesulfonamide (a) N-tert-Butyl-4-iso-butylbenzenesulfonamide Chlorosulfonic acid (28.6 mL, 0.43 mol) was added dropwise to stirred iso-butylbenzene (11.14 g, 0.083 mol) at 0° C.

The reaction mixture was then heated to 40° C. for 0.5 h, poured into ice-water (150 mL) and extracted with ethyl acetate (400 mL). The organic phase was washed with water and brine and dried over $MgSO_4$. The solvent was removed in vacuo and the residue was dissolved in $CHCl_3$ (50 mL). To this stirred solution, tert-butylamine (43.7 mL, 0.416 mol) was added dropwise. The reaction was heated to reflux for 10 min and then cooled to room temperature. The reaction mixture was then diluted with toluene (200 mL) and washed with water and brine. The organic phase was dried over $MgSO_4$ and the solvent was removed in vacuo. Purification using column chromatography with hexane:acetone (4:1) as eluent yielded the sub-title compound as a white solid (12.0 mg, 0.045 mol) in 54% yield.

IR (neat, $cm^{-1}$) v 3266, 2960, 2925, 2871, 1597, 1455

$^1$H NMR $\delta(CDCl_3)$: 7.84 (d, J=8.4 Hz, 2H), 7.27 (d, J=8.3 Hz, 2H), 5.11 (brs, 1H), 2.55 (d, J=7.3 Hz, 2H), 1.90 (m, 1H), 1.65 (m, 2H), 1.21 (s, 9H), 0.92 (d, J=6.6 Hz, 6H)

$^{13}$C NMR $\delta(CDCl_3)$: 146.4, 140.7, 129.9, 129.5, 126.8, 54.5, 45.1, 30.1, 22.3

MS (ESI$^+$) m/z: 270.0

Anal. Cald for $C_{14}H_{23}NO_2S$: C, 62.42; H, 8.61; N, 5.20; O, 11.88; S, 11.90; Found: C, 62.2; H, 8.5; N, 5.2

(b) 4-iso-Butyl-2-(N-tert-butylaminosulfonyl)benzene-3-boronic acid

To a solution of N-tert-butyl-4-iso-butyl-benzenesulfonamide (2.69 g, 10 mmol, see step (a)) in THF (50 mL), n-BuLi (15.6 mL, 1.6M, 25 mmol) was added dropwise at −78° C. under an atmosphere of $N_2$ (g). The temperature was allowed to rise gradually to 0° C. over 2 h and was then kept at that temperature for 30 min. The reaction mixture was then cooled to −40° C. and tri-iso-propylborate (4.6 mL, 20 mmol) was added. The reaction mixture was stirred overnight at ambient temperature and was quenched with 2M HCl (20 mL). The organic phase was separated and the water phase was extracted with EtOAc (3×100 mL). The combined organic phase was washed with brine and dried and concentrated in vacuo. The crude product was used in the next step without further purification.

MS (ESI$^+$) m/z: 314.0

(c) 2-(4-Imidazol-1-ylmethylphenyl)-4-iso-butyl-N-tert-butylbenzenesulfonamide The crude product from step (b) above (1.2 g, 3.83 mmol), 1-(4bromo-benzyl)-1H-imidazole (98.8 mg, 0.416 mmol, see Example 1(d) above), Pd(PPh$_3$)$_4$ (29 mg, 0.25 mmol), NaOH (3 mL, 1M, 3 mmol), toluene (15 mL) and ethanol (3 mL) were mixed under $N_2$ (g). The mixture was heated to reflux for 2 h. The reaction mixture was then diluted with ethyl acetate (150 mL) and washed with water and brine. The organic phase was dried over $MgSO_4$ and the solvent was removed in vacuo. Purification using column chromatography with $CHCl_3$:MeOH (20:1) as eluent yielded the sub-title compound (93.7 mg, 0.220 mmol) in 53% yield.

IR (neat, $cm^{-1}$) v 3379, 3293, 3153, 2955, 2868, 1701, 1596, 1505

$^1$H NMR $\delta(CDCl_3)$: 8.05 (d, J=8.1 Hz, 1H), 7.80 (s, 1H), 7.53 (d, J=8.2 Hz, 2H), 7.30 (m, 3H), 7.07 (m, 3H), 5.24 (s, 2H), 2.56 (d, J=7.1 Hz, 2H), 1.90 (m, 1H), 1.01 (s, 9H), 0.93 (d, J=6.6 Hz, 6H)

$^{13}$C NMR $\delta(CDCl_3)$: 146.2, 139.9, 138.9, 138.8, 136.7, 135.5, 132.8, 130.3, 128.4, 128.2, 127.9, 126.6, 119.5, 54.0, 50.6, 44.7, 29.4, 22.0

MS (ESI$^+$) m/z: 426.1

(d) 2-(4-Imidazo-1-1-ylmethylphenyl)-4-iso-butyl-benzene-sulfonamide

To a solution of 2-(4-imidazol-1-ylmethylphenyl)-4iso-butyl-N-tertbutylbenzene-sulfonamide (0.211 mmol, 90.0 mg, see step (c) above) in $CH_2Cl_2$ (5 mL) was added $BCl_3$ (1.5 mL, 1M, 1.5 mmol) under $N_2$ (g). The mixture was stirred for 0.5 h. Water (50 mL) was added and the mixture was extracted with ethyl acetate (3×50 mL). The combined organic phases were washed with brine and dried over $MgSO_4$ and the solvent was removed in vacuo. The crude product was used directly in the next step without further purification.

(e) N-Butyloxycarbonyl-2-(4-imidazol-1-ylmethylphenyl)-4-iso-butylbenzene-sulfonamide The crude product from step (d) above was dissolved in pyridine (2 mL, dried over 4 Å molecular sieve). Pyrrolidinopyridine (36 mg, 0.024 mmol) and butyl chloroformate (276 µL, 2.23 mmol) were added to the mixture, which was then stirred for 30 h under $N_2$ (g) at room temperature. The solvent was removed in vacuo and then co-evaporated with acetonitrile. Purification using column chromatography with $CHCl_3$:MeOH (10:1) as eluent yielded the title compound (66.7 mg, 0.142 mmol) in 68% yield (from 2-(4-imidazol-1-ylmethylphenyl)-4-iso-butyl-N-tert-butylbenzene-sulfonamide).

IR (neat, $cm^{-1}$) v 3129, 3058, 2956, 2869, 1737, 1658, 1466

$^1$H NMR $\delta(CDCl_3, CH_3OD)$: 8.14 (d, J=8.1 Hz, 1H), 7.72 (s, 1H), 7.36-7.19 (m, 6H), 7.04 (m, 3H), 5.19 (s, 2H), 3.98 (t, J=6.5 Hz, 2H), 2.56 (d, J=7.1 Hz, 2H), 1.93 (m, 1H), 1.41 (m, 2H), 1.21 (m, 2H), 0.93 (d, J=6.6 Hz, 6H), 0.85 (t, J=7.1 Hz, 3H)

$^{13}$C NMR $\delta(CDCl_3, CH_3OD)$: 151.8, 147.7, 140.4, 139.6, 137.1, 135.3, 134.9, 133.2, 130.5, 129.9, 128.6, 128.0, 127.0, 119.9, 66.3, 45.1, 30.6, 30.1, 22.4, 18.9, 13.6

MS (ESI$^+$) m/z: 470.1.

EXAMPLE 7

N-Butyloxycarbonyl-5-iso-butyl-3-(4-tetrazol-2-ylmethylphenyl)thiophene-2-sulfonamide

(a) 3-(4-Hydroxymethylphenyl)-5-iso-butyl-N-tert-butylthiophene-2-sulfonamide 5-iso-Butyl-2-(N-tert-butylaminosulfonyl)thiophene-3-boronic acid (319.3 mg, 1.00 mmol, see Example 1(c) above), 4-bromobenzyl alcohol (374.1 mg, 2.00 mmol), toluene (20 mL), ethanol (4 mL), NaOH (1.0M, 4 mL, 4 mmol) and Pd(PPh$_3$)$_4$ (34 mg, 0.030 mmol) were mixed together under $N_2$. The mixture was warmed to reflux for 2 hours and was then diluted with EtOAc (50 mL), washed with water and brine and dried over $MgSO_4$. The solvent was removed and the residue was separated by column chromatography using $CHCl_3$:MeOH (40:1) as eluent to give 289 mg of the sub-title compound (yield: 76%).

IR(neat): 3465, 3162, 2952, 2867, 1441 $cm^{-1}$ $^1$H NMR $\delta(CD_3OD)$: 7.59(2H, d, J=8.2 Hz), 7.45(2H, d, J=8.2 Hz), 6.75(1H, s), 4.75(2H, s), 4.11(1H, brs), 2.69(2H, d, J=7.1 Hz), 1.92(1H, m), 0.99(6H, d, J=7.2 Hz), 0.98(9H, s)

$^{13}$C NMR $(CD_3OD)$: 148.3, 142.9, 141.1, 134.2, 130.3, 128.9, 127.6, 126.8, 64.8, 54.5, 39.2, 30.5, 29.5, 22.1

MS(EI$^+$) m/z: 382.0

Anal. Calcd for $C_{19}H_{27}NO_3S_2$: C, 59.8; H, 7.3; N, 3.7. Found: C, 59.6; H, 7.0; N, 3.5

(b) 3-(4-Bromomethylphenyl)-5-iso-butyl-N-tert-butylthiophene-2-sulfonamide 3-(4Hydroxymethylphenyl)-5 -so-butyl-N-tert-butylthiophene-2-sulfonamide (280 mg, 0.734 mmol, see step (a) above) was dissolved in DMF (10 mL). PPh$_3$ (459.2 mg, 1.75 mmol) and CBr$_4$ (580.3, 1.75 mmol) were added to the resultant solution. The mixture was stirred for 24 h at room temperature and then diluted with ethyl acetate. The organic phase was washed with water (50 mL) and brine (50 mL) and then dried over MgSO$_4$. After removing the solvents, the residue was purified by column chromatography using hexane:acetone (5:1) as eluent to give the sub-title compound (314.9 mg, 0.709 mmol, 76% yield).

IR(neat): 3302, 2952, 2866, 1442 cm$^{-1}$
$^1$H NMR δ(CDCl$_3$): 7.62(2H, d, J=8.4 Hz), 7.48(2H, d, J=8.4 Hz), 6.75(1H, s), 4.56(2H, s), 4.11(1H, brs), 2.69(2H, d, J=7.1 Hz), 1.92(1H, m), 0.99(6H, d, J=7.2 Hz), 0.98(9H, s)
$^{13}$C NMR δ(CDCl$_3$): 148.5, 142.4, 138.2, 136.9, 135.1, 129.5, 129.1, 128.7, 54.6, 39.2, 32.8, 30.5, 29.5, 22.1
MS(EI$^+$) m/z: 445.8

(c) 5-iso-Butyl-N-tert-butyl-3-(4-tetrazol-2-ylmethylphenyl)thiophene-2-sulfonamide KOH (112.2 mg, 2.00 mmol, crushed pellets) was added to DMSO (10 mL, dried over 4A molecular sieve) and stirred for 5 min. Tetrazole (28.0 mg, 0.4 mmol) was added to the mixture, which was then stirred for 2 h. 3-(4-Bromomethylphenyl)-5-iso-butyl-N-tert-butylthiophene-2-sulfonamide (130 mg, 0.292 mmol, see step (b) above) was added, the mixture was cooled briefly and stirred for an additional hour before water (50 mL) was added. The reaction mixture was extracted with ethyl acetate (250 mL) and the extract was washed with water (2×50 mL) and brine (0 mL). The organic phase was dried over MgSO$_4$ and the solvent was removed in vacuo. The residue was purified on column chromatography using hexane:acetone (3:1) as eluent to give the sub-title compound (28.6 mg, 0.066 mmol, 23% yield).

IR(neat): 3328, 3134, 2980, 1501, 1466 cm$^{-1}$
$^1$H NMR δ(CDCl$_3$): 8.52(1H, s), 7.64(2H, d, J=8.3 Hz), 7.46(2H, d, J=8.3 Hz), 6.73(1H, s), 5.85(2H, s), 2.69(2H, d, J=7.1 Hz), 1.91(1H, m), 1.58(1H, s), 0.98(15H, brs)
$^{13}$C NMR δ(CDCl$_3$): 153.2, 148.5, 142.4, 136.8, 135.8, 133.2, 129.7, 128.8, 128.5, 56.3, 54.6, 39.2, 30.5, 29.5, 22.1
MS(EI$^+$) m/z; 434.0
Anal. Calcd for $C_{20}H_{27}N_5O_2S_2 \cdot xH_2O$: C, 53.2; H, 6.5; N, 15.5. Found: C, 53.7; H, 6.1; N, 15.2

(d) 5-iso-Butyl-3-(4tetrazol-2-ylmethylphenyl)thiophene-2-sulfonamide

To a solution of 5-iso-butyl-N-tert-butyl-3-(4-tetrazol-2-ylmethylphenyl)-thiophene-2-sulfonamide (42.1 mg, 0.111 mmol, see step (c) above) in CH$_2$Cl$_2$ (10 mL) was added BCl$_3$ (0.5 mL, 1M, 0.5 mmol) under N$_2$ (g). The reaction mixture was stirred for 0.5 h. Water (50 mL) was added and the mixture was extracted with ethyl acetate (3×50 mL). The combined organic phases were washed with brine and dried over MgSO$_4$ and the solvent was removed in vacuo. The crude product was used directly in the next step without further purification.

(e) N-Butyloxycarbonyl-5-iso-butyl-3-(4tetrazol-2-ylmethylphenyl)thiophene-2-sulfonamide The crude product from step (d) above was dissolved in pyridine (1 mL, dried over 4 Å molecular sieve). Pyrrolidinopyridine (14 mg, 0.0095 mmol) and butyl chloroformate (120 μL, 0.97 mmol) were added to the mixture, which was then stirred for 30 hours under N$_2$(g) at room temperature. The solvent was removed in vacuo and then co-evaporated with acetonitrile. Purification using column chromatography with CHCl$_3$:MeOH (35:1) as eluent yielded the title compound (24.9 mg, 0.052 mmol) in 54% yield (from 5-iso-butyl-N-tert-butyl-3-(4-tetrazol-2-ylmethylphenyl)thiophene-2-sulfonamide).

IR(neat): 3330, 2961, 2875, 1743, 1466 cm$^{-1}$
$^1$H NMR δ(CDCl$_3$): 8.49(1H, s), 7.68(1H, s), 7.48(2H, d, J=8.2 Hz), 7.40(2H, d, J=8.2 Hz), 6.73(1H, s), 5.82(2H, s), 4.07(2H, t, J=6.6 Hz), 2.70(2H, d, J=7.1 Hz), 1.91(1H, m), 1.50(2H, m), 1.24(2H, m), 0.98(6H, d, J=6.9 Hz), 0.87(3H, J=7.4 Hz)
$^{13}$C NMR δ(CDCl$_3$): 153.2, 151.8, 150.1, 145.6, 134.8, 133.4, 129.6, 129.3, 128.3, 66.9, 56.3, 39.2, 30.5, 30.4, 22.2, 18.7, 13.6
MS(EI$^+$) m/z: 478.0
Anal. Calcd for $C_{21}H_{27}N_5O_4S_2$: C, 52.8; H, 5.7; N, 14.7. Pound: C, 53.0; H, 5.8; N, 14.1

EXAMPLE 8

N-Butyloxycarbonyl-5-iso-butyl-3-(4-tetrazol-1-ylmethylphenyl)thiophene-2-sulfonamide

(a) 1-(4-Bromobenzyl)-1H-tetrazole

Dimethyl sulphoxide (10 mL, dried over 4 A molecular sieve) was added to potassium hydroxide (1.12 g, 0.02 mol, crushed pellets) and the mixture was stirred for 5 minutes. 1H-Tetrazole (0.35 g, 0.005 mol) was then added and the mixture was stirred for 2 hours. 4-Bromobenzyl bromide (1.87 g, 0.0075 mol) was added and the mixture was cooled briefly and stirred for a further hour before adding water (50 mL). The mixture was extracted with ether (3×80 mL) and each extract was washed with water (3×50 mL). The combined ether layers were dried over MgSO$_4$ and the solvent using removed in vacuo. The residue was chromatographed on silica gel with CHCl$_3$:MeOH (40:1) as eluent yielding the sub-title compound (0.98 g, yield: 82%).

$^1$H NMR δ(CDCl$_3$): 8.64(1H, s), 7.50(2H, d, J=8.4 Hz), 7.18(2H, d, J=8.4), 5.56(2H, s)
$^{13}$C NMR (CDCl$_3$): 142.4, 132.4, 131.8, 129.9, 123.4, 51.3
MS(ESI$^+$) m/z: 238.8
Anal. Calcd. for $C_8H_7BrN_4$: C, 40.2; H, 3.0; N, 23.4. Found: C, 40.3; H, 3.0; N, 23.4

(b) 5-iso-Butyl-N-tert-butyl-3-(4-tetrazol-1-ylmethylphenyl)thiophene-2-sulfonamide 5-iso-Butyl-2-(N-tert-butylaminosulfonyl)thiophene-3-boronic acid (401.0 mg, 1.256 mmol, see Example 1(c) above), 1-(4-bromobenzyl)-1H-tetrazole (199.4 mg, 0.834 mmol, see step (a) above), toluene (20 mL), ethanol (3.0 mL), NaOH (1.0M, 5.0 mL, 5.0 mmol) and Pd(PPh3)$_4$ (29.0 mg, 0.25 mmol) were mixed under N$_2$. The mixture was warmed to reflux for 2 hours. The mixture was diluted with EtOAc (20 mL), washed with water and brine, and dried over MgSO$_4$. The solvent was removed and the residue was separated by column chromatography using CHCl$_3$:MeOH (40:1) as eluent to give 222.4 mg of the sub-title compound (yield: 62%).

IR(neat): 3284, 3134, 2958, 2870, 1513, 1436 cm$^{-1}$ $^1$H NMR δ(CDCl$_3$): 8.71(1H, s), 7.64(2H, d, J=8.3 Hz), 7.40(2H, d, J=8.3 Hz), 6.74(1H, s), 5.65(2H, s), 2.67(2H, d, J=7.1 Hz), 1.94(1H, m), 0.99(15H, m)

$^{13}$C NMR δ(CDCl$_3$): 148.5, 142.6, 142.2, 136.8, 135.9, 133.1, 129.9, 128.8, 128.3, 54.6, 51.7, 39.2, 30.5, 29.5, 22.1

MS(ESI$^+$) m/z: 433

(c) 5-iso-Butyl-3-(4-tetrazol-1-ylmethylphenyl)thiophene-2-sulfonamide

BCl$_3$ (1.0 mL, 1M, 1.0 mmol) was added to a solution of 5-iso-butyl-N-tert-butyl-3-(4-tetrazol-1-ylmethylphenyl)thiophene-2-sulfonamide (177.0 mg, 0.408 mmol, see step (b) above) in CH$_2$Cl$_2$ (10 mL) under N$_2$ (g), and the reaction mixture was stirred for 0.5 h. Water (50 mL) was added and the mixture was extracted with ethyl acetate (3×50 mL). The combined organic phases were washed with brine, dried over MgSO$_4$ and the solvent was removed in vacuo. The crude product was used directly in the next step used without further purification.

(d) N-Butyloxycarbonyl-5-iso-butyl-3-(4-tetrazol-1-ylmethylphenyl)thiophene-2-sulfonamide The title compound was prepared (89.6 mg, 0.188 mmol, 46% yield (from 5-iso-butyl-N-tert-butyl-3-(4-tetrazol-1-ylmethylphenyl)thiophene-2-sulfonamide)) analogously to the procedure described in Example 7(e) above from the crude 5-iso-butyl-3-(4-tetrazol-1-ylmethylphenyl)-thiophene-2-sulfonamide from step (c) above.

IR(neat): 3135, 2959, 2875, 1747, 1464 cm$^{-1}$ $^1$H NMR δ(CDCl$_3$): 8.73(1H, s), 7.43(2H, d, J=7.7 Hz), 7.24(2H, d, J=7.7 Hz), 6.72(1H, s), 5.59(2H, s), 4.00(2H, brs), 2.69(2H, brs), 1.91(1H, m), 1.46(2H, m), 1.19(2H, m), 0.95(6H, d, J=6.9 Hz), 0.83(3H, J=6.8 Hz)

$^{13}$C NMR δ(CDCl$_3$): 151.8, 151.4, 145.3, 143.0, 134.8, 133.5, 129.6, 129.1, 127.8, 66.9, 51.4, 39.2, 30.9, 30.4, 22.2, 18.7, 13.6

MS(EI$^+$) m/z: 478.0

Anal. Calcd for C$_{21}$H$_{27}$N$_5$O$_4$S$_2$×1/2H$_2$O: C, 51.8; H, 5.8; N, 14.4. Found: C, 51.4; H, 5.6; N, 14.1

EXAMPLE 9

N-Butyloxycarbonyl-3-(4-[1,2,4]triazol-1-ylmethylphenyl)-5-iso-butylthiophene-2-sulfonamide

(a) 1-(4-Bromobenzyl)-1H-[1,2,4]triazole

DMF and KOH (3.3 g, 58 mmol) were stirred together at rt for 5 minutes before adding 1,2,4-triazole (1 g, 14.5 mmol). After a further 30 minutes, the reaction mixture was cooled to 0° C. and 1-bromo-4-bromomethyl-benzene (7.2 g, 29 mmol) was added dropwise over 5 minutes. The reaction mixture was heated to 60° C., then cooled to rt, extracted with ethyl acetate and water, and subsequently dried over K$_2$CO$_3$. The solvent was evaporated to yield yellow-white crystals, which, upon repeated recrystallisation, (ethylacetate/isohexane) yielded 0.60 g of the sub-title compound as white crystals (62% isolated yield).

$^1$H NMR δ(270 MHz, CDCl$_3$): 8.11 (s, 1H), 7.96 (s, 1H), 7.51-7.38 (m, 2H), 7.15-7.10 (m, 2H), 5.29 (s, 2H)

$^{13}$C NMR δ(67.8 MHz, CDCl$_3$): 152.2, 143.0, 133.5, 132.1, 129.5, 122.7, 52.8

MS m/z 238 (M$^+$+1)

(b) 3-(4-[1,2,4]Triazol-1-ylmethylphenyl)-5-iso-butyl-N-tert-butylthiophene-2-sulfonamide 5-iso-Butyl-2-(N-tert-butylaminosulfonyl)thiophene-3-boronic acid (0.479 g, 1.5 mmol, see Example 1(c) above), 1-(4-bromobenzyl)-1H-[1,2,4]triazole (0.238 g, 1 mmol, see step (a) above), Pd(OAc)$_2$ (15.7 mg, 0.03 mmol), triphenyl phosphine (15.7 mg, 0.06 mmol) and NaOH (0.16 g, 4 mmol) were dissolved in 4 mL of toluene/ethanol (4:1) in a thick walled glass tube, and were then heated to 80° C. for 1 h. The reaction mixture was cooled to rt, extracted with ethyl acetate and water and subsequently dried over K$_2$CO$_3$. The solvent was evaporated and the reaction mixture was separated on a silica column (dichloromethane+1% methanol to dichloromethane+4% methanol) to yield 0.288 g of the sub-title compound (65% yield).

$^1$H NMR δ(270 MHz; CDCl$_3$): 8.13 (s, 1H), 7.94 (s, 1H), 7.60-7.57 (m, 2H), 7.33-7.30 (m, 2H), 6.72 (s, 1H), 5.37 (s, 2H), 4.47 (s, 1H), 2.65, (d, J=7 Hz, 2H), 1.89 (sept J=7 Hz, 1H), 0.96 (s, 9H), 0.94 (d, J=7 Hz, 6H)

$^{13}$C NMR δ(67.8 MHz, CDCl$_3$): 152.1, 148.5, 143.1, 142.3, 136.6, 135.2, 134.8, 129.6, 128.8, 128.0, 54.5, 53.1, 39.1, 30.4, 29.4, 22.1

MS m/z 433 (M$^+$+1)

(c) 3-(4-[1,2,4]Triazol-1-ylmethylphenyl)-5-iso-butylthiophene-2-sulfonamide 3-(4-[1,2,4]Triazol-1-ylmethylphenyl)-5-iso-butyl-N-tert-butylthiophene-2-sulfonamide (146.4 mg, 0.34 mmol, see step (b) above) was mixed with BCl$_3$ (1M solution in hexane) (2 mL, 1.7 mmol) in 5 mL of dichloromethane at rt and stirred for 1 h. The reaction mixture was extracted with ethyl acetate and water and subsequently dried over K$_2$CO$_3$. The solvent was evaporated and the resultant product was sufficiently pure to be used directly in the next step.

(d) N-Butyloxycarbonyl-3-(4-[1,2,4]triazol-1-ylmethylphenyl)-5-iso-butylthiophene-2-sulfonamide 59 mg (0.16 mmol) of the crude 3-(4-[1,2,4]triazol-1-ylmethylphenyl)-5-iso-butylthiophene-2-sulfonamide from step (c) above was mixed with butyl 5 chloroformate (31 μL, 0.24 mmol) and 4-dimethylaminopyridine (2 mg, 16 μmol) in 5 mL of triethylamine at 0° C. The reaction mixture was stirred overnight and then diluted with ethyl acetate, washed with water and dried over K$_2$CO$_3$. The reaction mixture was then separated on a silica column (dichloromethane+15% methanol), circular chromatography lo (dichloromethane+10-15% methanol and preparative LC-MS to yield 7.0 mg of the title compound (9% isolated yield).

$^1$H NMR δ(270 MHz, CDCl$_3$): 8.11 (s, 1H), 7.98 (s, 1H), 7.50-7.47 (m, 2H), 7.29-7.26 (m, 2H), 6.74 (s, 1H), 5.39 (s, 2H), 4.05 (t, J=7 Hz, 2H), 2.71 (d, J=7 Hz, 2H), 1.95 (sept, J=7 Hz, 1H), 1.52 (pent, J=7 Hz, 2H), 1.26 (sext, J=7 Hz, 2H), 0.99 (d, J=7 Hz, 6H), 0.88 (t, J=7 Hz, 3H)

$^{13}$C NMR δ(67.8 MHz, CDCl$_3$): 151.9, 151.1, 145.1, 143.4, 134.7, 134.2, 131.6, 129.7, 129.0, 127.8, 66.3, 53.2, 39.2, 30.4, 30.3, 22.1, 18.7, 13.5

MS m/z (relative intensity 30 eV) 477 (M$^+$+1)

EXAMPLE 10

N-(Butylamino)carbonyl-3-(4-imidazol-1-ylmethylphenyl)-5-iso-butylthiophene-2-sulfonamide

(a) 1-(4-Bromobenzyl)-1H-imidazole

Dimethyl sulphoxide (20 mL, dried over 4 Å molecular sieves) was added to potassium hydroxide (2.24 g, 0.04 mol, crushed pellets) and the mixture was stirred for 5 min. Imidazole (0.5718 g, 0.0084 mol) was then added and the mixture was stirred for 2 hours. 4-Bromobenzyl bromide (3.25 g, 0.013 mol) was added and the mixture was cooled briefly and stirred for a further hour before adding water (20 mL). The mixture was extracted with ether (3×100 mL) and each extract was washed with water (3×50 mL). The combined ether layers were dried over CaCl$_2$ and the solvent was removed in vacuo. The residue was chromatographed on silica gel with CHCl$_3$/MeOH (30:1) plus 0.05% formic acid as eluent yielding the sub-title compound (1.275 g, yield: 53%).

$^1$H NMR δ(CDCl$_3$): 7.73 (m, 3H), 7.28 (m, 3H), 7.15 (m, 1H), 5.30 (s, 2H)

$^{13}$C NMR δ(CDCl$_3$): 136.8, 134.8, 131.5, 129.3, 128.4, 121.5, 118.7, 49.4

MS (ESI$^+$) m/z: 236.8

(b) 3-(4-Imidazol-1-ylmethylphenyl)-5-iso-butyl-N-tert-butylthiophene-2-sulfonamide 5-iso-Butyl-2-(N-tert-butylaminosulfonyl)thiophene-3-boronic acid (200.5 mg, 0.628 mmol, see Example 1(c) above), 1-(4-bromobenzyl)-1H-imidazole (98.8 mg, 0.416 mmol, see step (a) above), toluene (15 mL), ethanol (15 mL), NaOH (1.0M, 1.5 mL, 1.5 mmol) and Pd(PPh$_3$)$_4$ (14.5 mg, 0.125 mmol) were mixed under N$_2$. The mixture was warmed to reflux for 2 hours. The mixture was diluted with EtOAc (50 mL), washed with water and brine, and dried over MgSO$_4$. The solvent was removed and the residue was separated by column chromatography with chloroform:methanol (20:1) as eluent to give 113.9 mg of the sub-title compound (yield: 63.27%).

IR (neat, cm$^{-1}$) v 3060, 2996, 1507

$^1$H NMR δ(CDCl$_3$): 7.39 (s, 1H), 7.35 (d, J=8.1 Hz, 2H), 6.98 (d, J=8.1 Hz, 2H), 6.96 (s, 1H), 6.84 (s, 1H), 6.47 (s, 1H), 4.91 (s, 2H), 3.96 (s, 1H), 2.72 (brs, 1H), 2.42 (d, J=7.1 Hz, 2H), 1.64 (m, 1H), 0.73 (s, 9H), 0.72 (d, J=6.9 Hz, 6H)

$^{13}$C NMR (CDCl3): 148.6, 142.3, 137.2, 136.2, 135.1, 129.7, 129.4, 128.8, 127.4, 119.2, 54.6, 50.6, 39.2, 30.5, 29.5, 22.1

MS (ESI$^+$) m/z: 431.9

Anal. Calcd for C22H$_{29}$N$_3$O$_2$S$_2$: C, 58.8; H, 7.0; N, 9.4. Found: C, 58.7.0; H, 6.7; N, 9.1

(c) 3-(4-imidazol-1-ylmethylphenyl)-5-iso-butylthiophene-2-sulfonamide

To a solution of 3-(4-imidazol-1-ylmethylphenyl)-5-isobutyl-N-tert-butylthiophene-2-sulfonamide (0.097 mmol, 42.0 mg, see step (b) above) in CH$_2$Cl$_2$ (10 mL) was added BCl$_3$ (0.5 mL, 1M, 0.5 mmol) under N$_2$ (g). The mixture was stirred for 0.5 h. Water (50 mL) was added and the mixture was extracted with ethyl acetate (3×50 mL). The combined organic phases were washed with brine and dried over MgSO$_4$ and the solvent was removed in vacuo. The crude product was used directly in the next step without further purification.

(d) N-(Butylamino)carbonyl-3-(4-imidazol-1-ylmethylphenyl)-5-iso-butylthiophene-2-sulfonamide The crude product from step (c) above was dissolved in acetone (5 mL) under N$_2$ (g). NaOH (0.20 mL, 1M, 0.20 mmol) was added to the mixture, which was then stirred for 10 min. Butyl isocyanate (109 μL, 0.97 mmol) was then added and the mixture was stirred overnight at room temperature. The reaction mixture was then diluted with ethyl acetate (150 mL) and washed with water and brine. The organic phase was dried over MgSO$_4$ and the solvent was removed in vacuo. Purification using column chromatography with CHCl$_3$:MeOH (10:1) as eluent yielded the title compound (15.1 mg, 0.032 mmol) in 33% yield (from 3-(4-imidazol-1-ylmethylphenyl)-5-iso-butylthiophene-2-sulfonic acid tert-butylamide).

IR (neat, cm$^{-1}$) v 3261, 3120, 2957, 2869, 1701, 1514

$^1$H NMR δ(CDCl$_3$, CH$_3$OD): 7.64 (s, 1H), 7.49 (d, J=8.1 Hz, 2H), 7.11 (d, J=8.1 Hz, 2H), 6.97 (brs 1H), 6.90 (brs, 1), 6.72 (s, 1H), 6.24 (brs, 1H), 5.10 (s, 2H), 3.08 (m, 2H), 2.62 (d, J=7.1 Hz, 2H), 1.92 (m, 1H), 1.20 (m, 4H), 0.99 (d, J=6.6, 6H), 0.86 (t, J=7.1 Hz, 3H)

$^{13}$C NMR δ(CDCl$_3$, CH$_3$OD): 152.2, 150.0, 144.5, 137.0, 135.9, 134.4, 133.0, 129.7, 129.5, 128.1, 127.1, 119.5, 50.7, 39.9, 39.2, 31.6, 30.5, 22.2, 19.8, 13.7

MS (ESI$^+$) m/z: 475.2

EXAMPLE 11

N-Butylsulfonyl-3-(4-imidazol-1-ylmethylphenyl)-5-iso-butylthiophene-2-sulfonamide Crude 3-(4-imidazol-1-ylmethylphenyl)-5-iso-butylthiophene-2-sulfonamide (prepared according to the procedure described in Example 10(c) above) was dissolved in THF (3 mL) under N$_2$ (g). NaOH (1.0 mL, 1M, 1.0 mmol) was added to the mixture, which was then stirred for 10 min. Butanesulfonyl chloride (45 μL, 0.35 mmol) was then added, and the mixture was stirred for 24 h at room temperature. The reaction mixture was then diluted with ethyl acetate (150 mL) and washed with water and brine. The organic phase was dried over MgSO$_4$ and the solvent was removed in vacuo. The crude product was recrystallised from acetone to yield the title compound (31.7 mg, 0.064 mmol).

IR (neat, cm$^{-1}$) v 3133, 2959, 2871, 1576, 1543, 1514

$^1$H NMR δ(CDCl$_3$, CH$_3$OD): 8.70 (s, 1H), 7.64 (d, J=8.1 Hz, 2H), 7.08-7.20 (m, 5H), 6.59 (s, 1H), 5.06 (s, 2H), 3.08 (m, 2H), 2.57 (d, J=7.1 Hz, 2l), 1.67 (m, 1H), 1.65 (m, 2l1), 1.29 (m, 2H), 0.89-0.79 (m, 9H)

$^{13}$C NMR δ(CDCl$_3$, CH$_3$OD): 146.8, 140.9, 138.2, 136.8, 135.0, 131.9, 130.4, 128.6, 127.9, 121.2, 119.8, 54.0, 52.5, 38.9, 30.3, 25.6, 21.9; 21.4, 13.4

MS (ESI$^+$) m/z: 496.1

EXAMPLE 12

N-Butylsulfonyl-3-(4-imidazol-1-ylmethylphenyl)-5-iso-butylthiophene-2-carboxamide

(a) 2-iso-Butylthiophene

A solution of thiophene (6.00 g, 0.0714 mol) in 80 mL of THF (80 mL) was treated with n-BuLi (1.6 M in hexane, 54 mL, 0.0864 mol) at −78° C. The mixture was stirred at −40° C. for about 2 hours. The solution was then cooled to −78° C. again and treated with 2-methylpropyliodide (16.04 g, 0.0871 mol). The solution was stirred at 0° C. for 2 hours, and then overnight at room temperature for about 16 hours. The solution was treated with water (25 mL) and extracted with petroleum ether (3×25 mL). The organic layer was dried over magnesium sulfate and filtered. The crude product was purified by distillation (54-55° C. at 12 mmHg) to give the sub-title compound (3.0 g, 0.0213 mol) in 30% yield.

$^1$H NMR δ(CDCl$_3$): 7.14 (dd, J=5.1, 1.2 Hz, 1H), 6.95 (dd, J=5.1, 3.3 Hz, 1H), 6.79 (dd, J=3.3, 1.2 Hz, 1H), 2.72 (d, J=7.1 Hz, 2H), 1.92 (m, 1H), 0.97 (d, J=6.7 Hz, 3H)

$^{13}$C NMR δ(CDCl$_3$): 144.3, 126.5, 124.8, 123.0, 39.1, 30.8, 22.2

MS(EI$^+$) m/z: 140

(b) 5-iso-Butyl-N-tert-butylthiophene-2-carboxamide

To 2-iso-butylthiophene (1 g, 7.143 mmol, see step (a) above) in THF (15 mL) was added n-BuLi (1.6 M in hexane, 5.3 mL, 8.48 mmol) at −78° C. and the reaction mixture was stirred at 0° C. for 2 hours. tert-Butyl-isocyanate (897 µL, 7.86 mmol) was then added to the mixture at −78° C. The stirred solution was kept at 0° C. for an additional 2 hours. The reaction mixture was then quenched with H$_2$O (15 mL) and extracted with EtOAc (3×20 mL). The organic layer was dried over MgSO$_4$, concentrated and purified using silica gel column chromatography (10:90 petroleum ether-EtOAc) to give the sub-title compound (1.2 g, 5.01 mmol) as white needles in 70% yield.

$^1$H NMR δ(CDCl$_3$): 7.24 (d, J=3.6 Hz, 1H), 6.69 (d, J=3.6 Hz, 1H), 5.72 (brs, 1H), 2.65 (d, J=7.2 Hz, 2H), 1.88 (m, 1H), 1.44 (s, 9H), 0.93 (d, J=6.6 Hz, 3H)

$^{13}$C NMR δ(CDCl$_3$): 161.4, 149.2, 137.6, 127.5, 125.5, 51.8, 39.5, 30.7, 28.9, 22.1

IR(neat): 3215, 2924, 1620, 1550, 1464,cm$^{-1}$

Anal. Calcd. for C$_{13}$H$_{21}$NOS: C, 65.2; H, 8.8; N, 5.9. Found: C, 65.5; H, 8.9; N, 5.9.

MS(EI$^+$) m/z: 239

(c) 5-iso-Butyl-N-tert-butylthiophene-2-carboxamide-3-boronic acid

To a solution of 5-iso-butyl-N-tert-butylthiophene-2-carboxamide (from step (b) above; 0.5 g, 2.1 mmol) in THF (50 mL) was added 3.3 mL n-BuLi (1.6M in hexane, 3.3 mL, 5.28 mmol) at −78° C. The reaction mixture was slowly warmed to −20° C. and stirred for 4 hours. Tri-iso-propylborate (0.59 g, 3.14 mmol) was added to the mixture at −78° C. The solution was slowly warmed to room temperature and stirred overnight. The reaction was quenched with HCl(aq) (2M, 2 mL) and extracted with EtOAc (2×25 mL), washed with brine, dried with MgSO$_4$ and concentrated. The crude product was used in the next step without further purification.

MS(EI$^+$) m/z: 284

(d) 3-(4-imidazol-1-ylmethylphenyl)-5-iso-butyl-N-tert-butylthiophene-2-carboxamide 5-iso-Butyl-N-tert-butylthiophene-2-carboxamide-3-boronic acid (200 mg, 0.706 mmol, see step (c) above), 1-(4-bromobenzyl)-1H-imidazole (80 mg, 0.337 mmol), toluene (5 mL), ethanol (2 mL), NaOH (1.63 M, 0.84 mL, 1.38 mmol) and Pd(PPh$_3$)$_4$ (16.3 mg, 0.014 mmol) were mixed together under N$_2$. The resultant mixture was warmed to reflux for 2 hours. The mixture was diluted with EtOAc (50 mL), washed with water and brine, and dried over MgSO$_4$. The solvent was removed and the residue was separated by column chromatography with chloroform:methanol (95:5) as eluent to give 99 mg of the sub-title compound (yield: 74%).

$^1$H NMR δ(CDCl$_3$): 7.55 (br s, 1H), 7.41 (d, J=8.1 Hz, 2H), 7.24 (d, J=8.1 Hz, 2H), 7.09 (br s, 1H), 6.89 (br s, 1H), 6.63 (s, 1H), 5.25 (br s, 1H), 5.16 (s, 2H), 2.63 (d, J=6.9 Hz, 2H), 1.89 (m, 1H), 1.13 (s, 9H), 0.95 (d, J=6.6 Hz, 3H)

$^{13}$C NMR δ(CDCl$_3$): 161.4, 147.4, 140.2, 137.3, 136.3, 136.1, 133.9, 130.0, 129.8, 128.3, 127.6, 119.0, 51.4, 50.4, 39.3, 30.5, 28.4, 22.2

IR(neat): 3113 2930, 1645, 1512 cm$^{-1}$

MS(EI$^+$) m/z: 396

Anal. Calcd. for C$_{23}$H$_{29}$N$_3$OS+H$_2$O: C, 66.8; H, 7.6; N, 10.2. Found: C, 67.0; H, 7.6; N, 9.9.

(e) 3-(4-Imidazol-1-ylmethylphenyl)-5-iso-butylthiophene-2-carboxamide

Trifluoroacetic acid was added (2.5 mL) to 3-(4-imidazol-1-ylmethylphenyl)-5-iso-butyl-N-tert-butylthiophene,2-carboxamide (165 mg, 0.417 mmol, see step (d) above), and one drop (ca. 0.05 mL) of anisol was added to the reaction mixture. The mixture was stirred under a N$_2$ atmosphere for 30 hours and then evaporated and co-evaporated with acetonitrile. The crude product was purified by column chromatography (CH$_2$Cl$_2$:MeOH (85:15)) to give the sub-title compound (117 mg, 0.345 mmol) in 73% yield.

$^1$H NMR δ(CD$_3$OD): 9.05 (br s, 1H), 7.63 (br s, 1H), 7.55 (br s, 1H), 7.51 (d, J=8.4 Hz, 2H), 7.45 (d, J=8.4 Hz, 2H), 6.81 (s, 1H), 5.47 (s, 2H), 2.68 (d, J=7.1 Hz, 2H), 1.90 (m, 1H), 0.96 (d, J=6.6 Hz, 3H)

$^{13}$C NMR δ(CD$_3$OD): 167.1, 148.9, 144.1, 137.9, 136.6, 135.1, 131.2, 130.8, 130.1, 129.8, 123.3, 121.6, 53.4, 40.0, 31.8, 22.5

IR(neat): 3308, 2957, 1657, 1509, 1461

MS(EI$^+$) m/z: 340

Anal. Calcd. for C$_{19}$H$_{21}$N$_3$OS: C, 67.2; H, 6.2; N, 12.4. Found: C, 67.5; H, 6.4; N, 12.3.

(f) N-Butylsulfonyl-3-(4-imidazol-1-ylmethylphenyl)-5-iso-butylthiophene-2-carboxamide NaH (55%, 12 mg, 0.28 mmol) was added to a solution of 3-(4-imindazol-1-ylmethylphenyl)-5-iso-butylthiophene-2-carboxamide (46 mg, 0.136 mmol, see step (e) above) in THF (1 mL). The mixture was stirred at 50° C. for 0.5 hours. Butanesulfonyl chloride (29 µL, 0.223 mmol) was added dropwise and the reaction mixture was stirred at room temperature for 1 hour. The mixture was concentrated and purified using silica gel chromatography (CH$_2$Cl$_2$:MeOH, 9:1) to give 31 mg of the title compound as a white powder (yield: 50%).

$^1$H NMR δ(CDCl$_3$): 7.82 (br s, 1H), 7.32 (br s, 2H), 7.06 (d, J=7.4 Hz, 2H), 6.95 (br s, 2H), 6.64 (s, 1H), 5.09 (br s, 2H), 4.79 (br s, 1H), 2.97 (br s, 2H), 2.62 (d, J=6.9 Hz, 2H), 1.90 (m, 1H), 1.65 (br s, 2H), 1.29 (m, 2H), 0.95 (d, J=6.5 Hz, 6H), 0.81 (t, J=6.6 Hz, 3H)

$^{13}$C NMR δ(CDCl$_3$): 166.4, 148.9, 144.3, 137.3, 136.4, 134.8, 132.2, 130.0, 129.4, 127.2, 119.9, 53.2, 51.0, 39.5, 30.5, 25.4, 22.3, 21.5, 13.6

MS(EI$^+$) m/z: 460

Anal. Calcd. for C$_{23}$H$_{29}$N$_3$O$_3$S$_2$+H$_2$O: C, 57.8; H, 6.5; N, 8.8. Found: C, 58.1; H, 6.4; N, 8.3.

IR(neat): 3482, 3118, 2958, 1558, 1456 cm$^{-1}$

EXAMPLE 13

The following compounds were also prepared in accordance with techniques described herein:

(i) N-butyloxycarbonylbutyl-2-(4-imidazol-1-ylmethylphenyl)benzenesulfonamide $^1$H NMR δ(CDCl$_3$),: 8.95 (brs, 1H), 8.20 (d, J=8.3 Hz, 1H), 7.66 (brs, 1H), 7.38 (d, J=8.0 Hz, 2H), 7.34 (dd, J=8.3, 1.6 Hz, 1H), 7.11 (d, J=8.0 Hz, 2H,), 7.05 (d, J=1.6 Hz, 1H), 6.83 (brs, 2H), 5.10 (s, 2H), 4.00 (t, J=6.5, 2H), 2.67 (t, J=7.5Hz, 2H), 1.62 (m, 2H), 1.48 (m, 2H), 1.36 (m, 2H), 1.22 (m, 2H), 0.92 (t, J=7.2 Hz, 3H), 0.86 (t, J=7.3 Hz, 3H)
$^{13}$C NMR δ(CDCl$_3$): 151.9, 148.5, 140.2, 139.9, 136.7, 135.1, 134.7, 132.3, 130.8, 129.9, 127.7, 127.2, 126.9, 119.2, 65.9, 50.9, 35.4, 33.0, 30.5, 22.4, 18.8, 13.8, 13.6

(ii) N-(2-methoxyethyloxy)carbonyl-3-(4-imidazol-1-ylmethylphenyl)-5-iso-butylthiophene-2-sulfonamide $^1$H NMR δ(20% CD$_3$OD in CDCl$_3$): 8.00 (brs, 1H), 7.56 (d, J=7.7 Hz, 2H), 7.19 (d, J=7.7 Hz, 2H), 7.07 (brs, 2H), 6.75 (s, 1H), 5.20 (s, 2H), 4.14 (brt, J=4.5 Hz, 2H), 3.52 (brt, J=6.9 Hz, 2H), 3.32 (s, 3H), 2.70 (d, J=7.1 Hz, 2H), 1.94 (m, 1H), 0.99 (d, J=6.4 Hz, 6H)
$^{13}$C NMR δ(20% CD$_3$OD in CDCl$_3$): 153.1, 149.7, 144.0, 136.1, 134.8, 134.6, 132.8, 129.6, 128.8, 127.0, 125.6, 119.8, 70.0, 64.1, 58.2, 50.9, 38.9, 30.2, 21.8

(iii) N-ethyloxycarbonyl-3-(4-imidazol-1-ylmethylphenyl)-5-iso-butylthiophene-2-sulfonamide $^1$H NMR δ(20% CD$_3$OD in CDCl$_3$): 7.78 (brs, 1H), 7.55 (d, J=7.8 Hz, 2H), 7.24 (d, J=7.8 Hz, 2H), 7.07 (brs, 2H), 6.77 (s, 1H), 5.22 (s, 2H), 4.06 (q, J=7.1 Hz, 2H), 2.71 (d, J=7.1 Hz, 2H), 1.95 (m, 1H), 1.17 (t, J=7.1 Hz, 3H), 0.99 (d, J=6.4 Hz, 6H)
$^{13}$C NMR δ(20% CD$_3$OD in CDCl$_3$): 153.0, 150.7, 145.1, 137.2, 135.9, 135.0, 132.7, 130.1, 129.5, 127.9, 127.6, 120.2, 62.6, 49.6, 39.5, 30.8, 22.3, 14.3

(iv) N-tert-butyloxycarbonyl-3-(4-imidazol-1-ylmethylphenyl)-5-iso-butylthiophene-2-sulfonamide $^1$H N δ(10% CD$_3$OD in CDCl$_3$): 7.65 (brs, 1H), 7.39 (d, J=7.9 Hz, 2H), 7.11 (d, J=7.9 Hz, 2H), 6.94 (brs, 2H), 6.65 (s, 1H), 5.09 (s, 2H), 2.59 (d, J=7.1 Hz, 2H), 1.82 (m, 1H), 1.22 (s, 9H), 0.87 (d, J=6.6 Hz, 6H)
$^{13}$C NMR δ(10% CD$_3$OD in CDCl$_3$): 150.5, 149.5, 144.6, 136.6, 135.5, 134.2, 131.7, 129.5, 129.0, 128.0, 127.1, 119.6, 83.0, 50.6, 39.0, 30.3, 27.5, 21.9

(v) N-butyloxycarbonyl-3-[4-(4-methylimidazol-1-ylmethyl)phenyl]-5-iso-butylthiophene-2-sulfonamide $^1$H NMR δ(CDCl$_3$): 8.22 (s, 1H), 7.55 (d, J=8.2 Hz, 2H), 7.27 (d, J=7.9 Hz, 2H), 6.84 (s, 1H), 6.74 (s, 1H), 5.18 (s, 2H), 4.03 (t, J=6.6 Hz, 2H), 2.71 (d, J=6.9 Hz, 2H), 2.24 (s, 3H), 1.94 (m, 1H), 1.51 (m, 2H), 1.28 (m, 2H), 1.00 (d, J=6.6 Hz, 6H), 0.87 (t, J=7.4 Hz, 3H)
$^{13}$C NMR δ(CDCl$_3$): 152.4, 150.5, 144.6, 135.2, 134.5, 132.6, 130.0, 129.1, 127.8, 117.1, 116.9, 66.3, 51.7, 39.3, 30.6, 22.3, 18.9, 13.6, 11.5

(vi) N-butyloxycarbonyl-3-(4-pyrazol-1-ylmethylphenyl)-5-iso-butylthiophene-2-sulfonamide $^1$H NMR δ(CDCl$_3$): 0.84 (t, J=7.3 Hz, 3H), 0.95 (d, J=6.6 Hz, 6H), 1.22 (m, 2H), 1.48 (m, 2H), 1,90 (m, 1H), 2.66 (d, J=6.9 Hz, 2H), 4.01 (t, J=6.6 Hz, 2H), 5.26 (s, 2H), 6.23 (s, 1H), 6.69 (s, 1H), 7.02 (d, J=8.3 Hz, 2H), 7,37 (m, 3H), 7.48 (s, 1H)
$^{13}$C NMR δ(CDCl$_3$): 13.6, 18.7, 22.2, 30.4, 39.2, 55.1, 66.5, 106.0, 127.3, 129.3, 129.6, 133.7, 136.9, 139.4, 145.7, 150.6, 151.3

(vii) N-butyloxycarbonyl-3-[4-(3-trifluoromethylpyrazol-1-ylmethyl)-phenyl]-5-iso-butylthiophene-2-sulfonamide $^1$H NMR δ(CDCl$_3$): 7.66 (s, 1H), 7.50 (s, 1H), 7.42 (d, J=8.1 Hz, 2H), 7.23 (d, J=8.2 Hz, 2H), 6.74 (s, 1H), 6.59 (d, J=2.1 Hz, 1H), 5.40 (s, 2H), 4.03 (t, J=6.6 Hz, 2H), 2.71 (d, J=6.9 Hz, 2H), 1.96 (m, 1H), 1.49 (m, 2H), 1.25 (m, 2H), 0.99 (d, J=6.6 Hz, 6H), 0.87 (t, J=7.4 Hz, 3H)
$^{13}$C NMR δ(CDCl$_3$): 151.8, 150.2, 146.0, 143.6, 142.5, 141.8, 139.4, 136.0, 134.0, 131.1, 130.6, 129.4, 127.5, 123.2, 119.2, 66.9, 56.1, 39.3, 30.5, 22.2, 18.7, 13.5

(viii) N-(N-butyl-N-methylamino)carbonyl-3-(4-imidazol-1-ylmethylphenyl)-5-iso-butylthiophene-2-sulfonamide $^1$H NMR δ(CDCl$_3$): 8.18 (brs, 1H), 7.84 (brs, 1H), 7.46 (d, J=8.2 Hz, 2H), 7.16 (d, J=8.2 Hz, 2H), 7.06 (brs, 1H), 6.99 (brs, 1H), 6.68 (s, 1H), 3.07 (brt, 2H), 2.67 (d, J=7.1 Hz, 2H), 2.56 (brs, 3H), 1.91 (m, 1H), 1.35 (m, 2H), 1.19 (m, 2H), 0.96 (d, J=6.6 Hz, 6H), 0.84 (t, J=7.2 Hz, 3H)
$^{13}$C NMR δ(CDCl$_3$): 153.6, 149.8, 143.3, 136.9, 135.5, 135.1, 134.2, 129.6, 128.7, 127.2, 126.8, 119.8, 51.0, 48.5, 39.3, 34.3, 30.4, 29.7, 22.3, 19.8, 13.8

(ix) N-butyloxycarbonyl-3-(4-imidazol-1-ylmethylphenyl)-5-(2-methoxyethyl)thiophene-2-sulfonamide $^1$H NMR δ(5% CD$_3$OD in CDCl$_3$): 7.86 (brs, 1H), 7.51 (d, J=7.9 Hz, 2H), 7.18 (d, J–7.9 Hz, 2H), 7.05 (brs, 1H), 6.99 (brs, 1H), 6.83 (s, 1H), 5.18 (s, 2H), 4.03 (t, J=6.5 Hz, 2H), 3.67 (t, J=6.2 Hz, 2H), 3.10 (t, J=6.2 Hz, 2H), 1.52 (m, 2H), 1.26 (m, 2H), 0.88 (t, J=7.3 Hz, 3H)
$^{13}$C NMR δ(5% CD$_3$OD in CDCl$_3$): 151.7, 148.1, 144.7, 136.9, 135.2, 134.8, 133.0, 129.9, 129.4, 127.4, 127.2, 119.8, 72.0, 66.3, 58.8, 51.1, 30.7, 30.5, 18.8, 13.6

EXAMPLE 14

Title compounds of the Examples were tested in Tests A and B above and were found to exhibit an affinity for AT2 receptors of less than Ki=100 nM (e.g. less than 50 nM) and an affinity to AT1 receptors of more than Ki=500 nM (e.g. more than 1 μM).

EXAMPLE 15

Title compounds of the Examples were tested in Test C above and were found to stimulate markedly mucosal alkalisation. This effect was blocked by co-administration of the selective AT2 receptor antagonist PD123319 (Sigma Chemical Company).

The invention claimed is:

1. A method of treatment of a condition, which method comprises administration of a therapeutically effective amount of a compound of formula I,

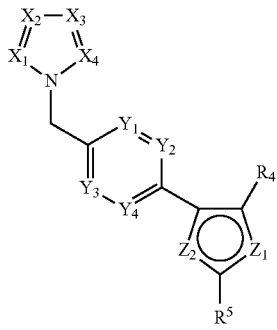

wherein
$X_1$ represents —C($R^1$)—;
$X_2$ represents —N—;
$X_3$ represents —C($R^2$)—;
$X_4$ represents —C($R^3$)—;
$R^1$ represents H;
$R^2$ and $R^3$ independently represent H, $C_{1-6}$ alkyl, $C_{1-6}$ alkoxy, $C_{1-6}$ alkoxy-$C_{1-6}$-alkyl or halo;
$Y_1$, $Y_2$, $Y_3$, and $Y_4$ independently represent —CH— or —CF—;
$Z_1$ represents —CH—, —O—, —S—, —N— or —CH=CH—;
$Z_2$ represents —CH—, —O—, —S— or —N—;
provided that:
(a) $Z_1$ and $Z_2$ are not the same;
(b) when $Z_1$ represents —CH=CH—, then $Z_2$ may only represent —CH— or —N—; and
(c) other than in the specific case in which $Z_1$ represents —CH=CH—, and $Z_2$ represents —CH—, when one of $Z_1$ and $Z_2$ represents —CH—, then the other represents —O— or —S—;
$R^4$ represents —S(O)$_2$N(H)C(O)$R^6$, —S(O)$_2$N(H)S(O)$_2R^6$, —C(O)N(H)S(O)$_2R^6$, or, when $Z_1$ represents —CH=CH—, $R^4$ may represent —N(H)S(O)$_2$N(H)C(O)$R^7$ or —N(H)C(O)N(H)S(O)$_2R^7$;
$R^5$ represents $C_{1-6}$ alkyl, $C_{1-6}$ alkoxy, $C_{1-6}$ alkoxy-$C_{1-6}$-alkyl or di-$C_{1-3}$-alkylamino-$C_{1-4}$-alkyl;
$R^6$ represents $C_{1-6}$ alkyl, $C_{1-6}$ alkoxy, $C_{1-6}$ alkoxy-$C_{1-6}$-alkyl, $C_{1-3}$ alkoxy-$C_{1-6}$-alkoxy, $C_{1-6}$ alkylamino or di-$C_{1-6}$ alkylamino; and
$R^7$ represents $C_{1-6}$ alkyl,
or a pharmaceutically acceptable salt thereof, to a person suffering from such a condition, wherein the condition is hypertension or hypertrophy.

2. The method as claimed in claim 1, wherein the condition is pulmonary hypertension, renal hypertension, or cardiac hypertrophy.

* * * * *